United States Patent
Abbondanza et al.

(10) Patent No.: US 11,856,806 B2
(45) Date of Patent: Dec. 26, 2023

(54) DISUBSTITUTED DL ARYLOXYBENZOH ETERODI AZOLE COMPOUNDS

(71) Applicant: ENI S.P.A., Rome (IT)

(72) Inventors: Luigi Abbondanza, Novara (IT);
Antonio Alfonso Proto, Novara (IT);
Giuliana Schimperna, Novara (IT)

(73) Assignee: ENI S.P.A., Rome (IT)

( * ) Notice: Subject to any disclaimer, the term of this patent is extended or adjusted under 35 U.S.C. 154(b) by 425 days.

(21) Appl. No.: 17/286,621

(22) PCT Filed: Oct. 18, 2019

(86) PCT No.: PCT/IB2019/058892
§ 371 (c)(1),
(2) Date: Apr. 19, 2021

(87) PCT Pub. No.: WO2020/079654
PCT Pub. Date: Apr. 23, 2020

(65) Prior Publication Data
US 2021/0367176 A1    Nov. 25, 2021

(30) Foreign Application Priority Data
Oct. 19, 2018 (IT) .................. 102018000009633

(51) Int. Cl.
*H02S 40/22* (2014.01)
*C09K 11/06* (2006.01)
(Continued)

(52) U.S. Cl.
CPC .......... *H10K 30/87* (2023.02); *C07D 417/14* (2013.01); *C09K 11/06* (2013.01); *H02S 40/22* (2014.12);
(Continued)

(58) Field of Classification Search
CPC .... H10K 30/87; H10K 85/655; H10K 85/657; H02S 40/22; C07D 417/14; C09K 11/06; C09K 2211/1007; C09K 2211/1019
See application file for complete search history.

(56) References Cited

U.S. PATENT DOCUMENTS
2017/0250350 A1* 8/2017 Abbondanza ........ C07D 417/14

FOREIGN PATENT DOCUMENTS
CN    107001353 A    8/2017
WO    2011048548 A1    4/2011
(Continued)

OTHER PUBLICATIONS
International Search Report dated Feb. 25, 2019 for PCT application No. PCT/IB2019/050151.
(Continued)

*Primary Examiner* — Jayne L Mershon
(74) *Attorney, Agent, or Firm* — Ruggiero McAllister & McMahon LLC

(57) ABSTRACT
There is a disubstituted diaryloxybenzoheterodiazole compound having general formula (I):
(Continued)

Esempio = Example
Esempio comparativo = Comparative example

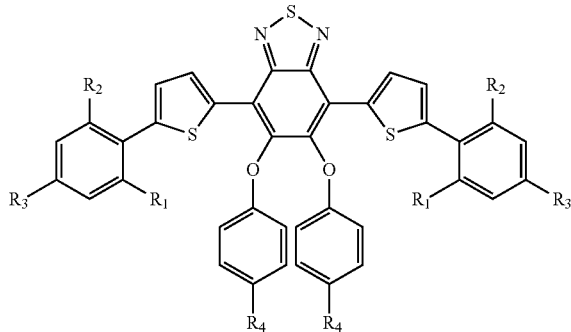

(I)

This disubstituted diaryloxybenzoheterodiazole compound having general formula (I) may advantageously be used as a spectrum converter in luminescent solar concentrators ("Luminescent Solar Concentrators"—LSCs) which, in turn, are capable of improving the performance of photovoltaic devices (or solar devices) selected, for example, from photovoltaic cells (or solar cells), photovoltaic modules (or solar modules), on either a rigid or flexible support.

9 Claims, 2 Drawing Sheets

(51) Int. Cl.
C07D 417/14 (2006.01)
H10K 30/87 (2023.01)
H10K 85/60 (2023.01)

(52) U.S. Cl.
CPC ......... *H10K 85/655* (2023.02); *H10K 85/657* (2023.02); *C09K 2211/1007* (2013.01); *C09K 2211/1018* (2013.01)

(56) References Cited

FOREIGN PATENT DOCUMENTS

| WO | 2011048548 A8 | 4/2011 |
| WO | 2012007834 A1 | 1/2012 |
| WO | 2016046310 A1 | 3/2016 |
| WO | 2016046319 A1 | 3/2016 |
| WO | 2017081645 A1 | 5/2017 |
| WO | 2018055074 A1 | 3/2018 |

OTHER PUBLICATIONS

Chinese First Office Action dated Apr. 21, 2023 from corresponding Chinese Patent Application No. 201980068884.5, 12 pages.
International Search Report dated Dec. 6, 2019 for PCT application No. PCT/IB2019/058892.
Written Opinion dated Dec. 6, 2019 for PCT application No. PCT/IB2019/058892.

\* cited by examiner

Esempio = Example

Esempio comparativo = Comparative example

Esempio = Example

Esempio comparativo = Comparative example

DISUBSTITUTED DI ARYLOXYBENZOH ETERODI AZOLE COMPOUNDS

CROSS-REFERENCE TO RELATED APPLICATIONS

The present application claims priority on PCT Application No. PCT/IB2019/058892, filed Oct. 18, 2019, which claims priority based on Italy Patent Application No. 102018000009633, filed Oct. 19, 2018, both of which are incorporated herein by reference in their entireties.

FIELD OF THE DISCLOSURE

The present disclosure relates to a disubstituted diaryloxybenzoheterodiazole compound. More specifically, the present disclosure relates to a diaryloxybenzoheterodiazole compound disubstituted with thiophene groups substituted with a phenyl group, said phenyl group being substituted with at least one phenoxy group.

Said diaryloxybenzoheterodiazole compound disubstituted with thiophene groups substituted with a phenyl group, said phenyl group being substituted with at least one phenoxy group, may advantageously be used as a spectrum converter in luminescent solar concentrators ("Luminescent Solar Concentrators"—LSCs) which, in turn, are capable of improving the performance of photovoltaic devices (or solar devices) selected, for example, from photovoltaic cells (or solar cells), photovoltaic modules (or solar modules), on either a rigid or flexible support.

The present disclosure also relates to a luminescent solar concentrator ("Luminescent Solar Concentrator"—LSC) including at least one diaryloxybenzoheterodiazole compound disubstituted with thiophene groups substituted with a phenyl group, said phenyl group being substituted with at least one phenoxy group, as well as a photovoltaic device (or solar device) comprising said luminescent solar concentrator ("Luminescent Solar Concentrator"—LSC).

DESCRIPTION OF THE RELATED ART

One of the main limitations to the use of solar energy is the ability of photovoltaic devices (or solar devices) to optimally absorb only radiation with wavelengths that fall within a narrow spectral range.

With a spectral range of solar radiation extending from wavelengths of about 300 nm to wavelengths of about 2500 nm, crystalline silicon-based photovoltaic cells (or solar cells), for example, have an optimal absorption zone (effective spectrum) in the range 900 nm-1100 nm, while polymer photovoltaic cells (or solar cells) are susceptible to damage when exposed to radiation of wavelength less than about 500 nm, due to induced photodegradation phenomena that become significant below this limit. Typically the efficiency of state-of-the-art photovoltaic devices (or solar devices) is at a maximum in the region of the spectrum ranging from 570 nm to 680 nm (yellow-orange).

The inconveniences mentioned above result in photovoltaic devices (or solar devices) having a limited external quantum efficiency (EQE), defined as the ratio between the number of electron-hole pairs generated in the semiconductor material of photovoltaic devices (or solar devices) and the number of photons incident on such photovoltaic devices (or solar devices).

To improve the external quantum efficiency (EQE) of photovoltaic devices (or solar devices), instruments have been developed that, when placed between the source of light radiation (the sun) and photovoltaic devices (or solar devices), selectively absorb the incident radiation having wavelengths outside the effective spectrum of these photovoltaic devices (or solar devices), emitting the absorbed energy in the form of photons of wavelength within the effective spectrum. Said instruments are referred to luminescent solar concentrators ("Luminescent Solar Concentrators"—LSCs). When the energy of the photons re-emitted by luminescent solar concentrators ("Luminescent Solar Concentrators"—LSCs) is higher than that of the incident photons, the photoluminescence process, including the absorption of solar radiation and the subsequent re-emission of photons with a shorter wavelength, is also referred to as an "up-conversion" process. On the contrary, when the energy of the photons emitted by the luminescent solar concentrators ("Luminescent Solar Concentrators"—LSCs) is lower than that of the incident photons, the photoluminescence process is referred to as a "down-conversion" (or "down-shifting") process.

Generally, said luminescent solar concentrators ("Luminescent Solar Concentrators"—LSCs) consist of large sheets of a material transparent to solar radiation (for example, polymer or inorganic glasses), within which fluorescent compounds that act as spectrum converters are dispersed, or chemically bound to said material. As a result of the optical phenomenon of total reflection, the radiation emitted by the fluorescent compounds is "guided" towards the thin edges of the plate wherein it is concentrated on photovoltaic cells (or solar cells) placed there. In this way large areas of low-cost materials (photoluminescent sheets) may be used to concentrate light on small areas of high-cost materials [photovoltaic cells (or solar cells)]. Fluorescent compounds may be deposited on the glass support in the form of a thin film or, as in the case of polymer materials, may be dispersed within the polymer matrix. Alternatively, the polymer matrix may be directly functionalized with fluorescent chromophore groups.

Ideally, to be used in spectrum converters, fluorescent compounds must have the following characteristics:
  high luminescence quantum efficiency (Φ) [(Φ) is defined according to equation (1) below reported as the ratio between the number of photons emitted and the number of photons absorbed by a luminescent molecule per unit of time, and has a maximum value of 1:
  (Φ)=number of photons emitted/number of photons absorbed (1);
  wide absorption band in the spectral region wherein the photovoltaic device (or solar device) is poorly efficient;
  high absorption coefficient;
  narrow emission band in the spectral region wherein the photovoltaic device (or solar device) is most efficient;
  well-separated absorption and emission bands to avoid or minimize self-absorption phenomena.

It is well known that some benzothiadiazole compounds, in particular 4,7-di-(thien-2'-yl)-2,1,3-benzothiadiazole (DTB), are fluorescent compounds that may be used in the construction of luminescent solar concentrators ("Luminescent Solar Concentrators"—LSCs). Such compounds have been described in the international patent application WO 2011/048458 in the name of the Applicant.

4,7-Di-(thien-2'-yl)-2,1,3-benzothiadiazole (DTB) is characterized by an emission centered around 579 nm, value which corresponds to an energy well above the minimum operating threshold of photovoltaic cells (or solar cells), a threshold that, for example, corresponds to a wavelength of about 1100 nm for the most popular photovoltaic cells (or solar cells), based on silicon. In addition, its absorption of light radiation is intense and extends over a relatively wide wavelength range, approximately ranging from 550 nm (the wavelength of green radiation) and the ultraviolet. Finally, in dichloromethane solution, 4,7-di-(thien-2'-yl)-2,1,3-benzothiadiazole (DTB) has a Stokes shift of 134 nm, much higher than those of most of the commercial products proposed so far for use in luminescent solar concentrators ("Luminescent Solar Concentrators"—LSCs).

For these reasons the use of 4,7-di-(thien-2'-yl)-2,1,3-benzothiadiazole (DTB) has made it possible to produce luminescent solar concentrators ("Luminescent Solar Concentrators"—LSCs) of excellent quality.

However, while absorbing a significant part of the solar spectrum, 4,7-di-(thien-2'-yl)-2,1,3-benzothiadiazole (DTB) has a modest absorption in regions with longer wavelengths, corresponding to yellow and red radiations, which, therefore, cannot be converted into other radiations more effectively exploited by the photovoltaic cell (or solar cell).

International patent application WO 2016/046319 in the name of the Applicant describes a disubstituted diaryloxybenzoheterodiazole compound having general formula (I):

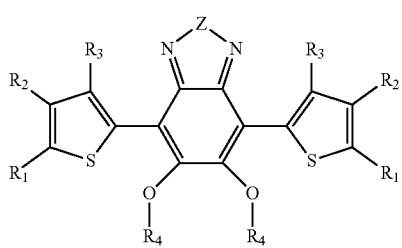

wherein:

Z represents a sulfur atom, an oxygen atom, a selenium atom; or an $NR_5$ group wherein $R_5$ is selected from $C_1$-$C_{20}$, preferably $C_1$-$C_8$, linear or branched alkyl groups, or from optionally substituted aryl groups;

$R_1$, $R_2$ and $R_3$, which are the same as or different from each other, represent a hydrogen atom; or are selected from $C_1$-$C_{20}$, preferably $C_1$-$C_8$, linear or branched alkyl groups, optionally containing heteroatoms, optionally substituted cycloalkyl groups, optionally substituted aryl groups, optionally substituted $C_1$-$C_{20}$, preferably $C_1$-$C_8$, linear or branched alkoxy groups, optionally substituted phenoxy groups, —$COOR_6$ groups wherein $R_6$ is selected from $C_1$-$C_{20}$, preferably $C_1$-$C_8$, linear or branched alkyl groups, or is a cyano group;

or $R_1$ and $R_2$ may be bonded together so as to form, together with the carbon atoms to which they are bonded, a saturated, unsaturated or aromatic cyclic or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

or $R_2$ and $R_3$ may be bonded together so as to form, together with the carbon atoms to which they are bonded, a saturated, unsaturated, or aromatic cyclic or a polycyclic system containing 3 to 14 carbon atoms, preferably 4 to 6 carbon atoms, optionally containing one or more hetero-atoms such as, for example, oxygen, sulfur, nitrogen, silicon, phosphorus, selenium;

$R_4$, which are the same as or different from each other, are selected from optionally substituted aryl groups.

The abovementioned disubstituted diaryloxybenzoheterodiazole compound is said to be advantageously used in the construction of luminescent solar concentrators ("Luminescent Solar Concentrators"—LSCs).

The Applicant was therefore faced with the problem of finding compounds capable of providing comparable or even greater performance, in particular in terms of the power generated by the photovoltaic devices (or solar devices) wherein they are used, both in comparison with known benzothiadiazole compounds and in comparison with the disubstituted dibenzoheterodiazole compounds specifically described in the above-mentioned international patent application WO 2016/046319.

SUMMARY OF THE DISCLOSURE

The Applicant has now found that some of the disubstituted diaryloxybenzoheterodiazole compounds not specifically described in the above-mentioned international patent application WO 2016/046319, in particular diaryloxybenzoheterodiazole compounds disubstituted with thiophene groups substituted with a phenyl group, said phenyl group being substituted with at least one phenoxy group, having the specific general formula (I) below reported, are able to provide the performance mentioned above. Said disubstituted diaryloxybenzoheterodiazole compounds may advantageously be used as spectrum converters in luminescent solar concentrators ("Luminescent Solar Concentrators"—LSCs) which, in turn, are capable of improving the performance of photovoltaic devices (or solar devices) selected, for example, from photovoltaic cells (or solar cells), photovoltaic modules (or solar modules), on either a rigid or flexible support. More specifically, these disubstituted diaryloxybenzoheterodiazole compounds are able to provide comparable or even higher performance, particularly in terms of power generated by the photovoltaic devices wherein they are used, in comparison to both known benzothiadiazole compounds and the disubstituted diaryloxybenzoheterodiazole compounds specifically described in above-mentioned international patent application WO 2016/046319.

The object of the present disclosure is therefore a disubstituted diaryloxybenzoheterodiazole compound having general formula (I):

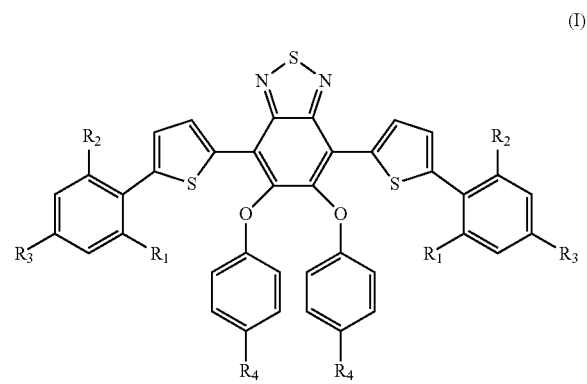

wherein:

$R_1$, $R_2$ and $R_3$, which are the same as or different from each other, represent a hydrogen atom; or represent a halogen atom such as, for example, chlorine, bromine, fluorine, iodine, preferably fluorine; or are selected from optionally halogenated linear or branched $C_1$-$C_{12}$, preferably $C_1$-$C_8$, alkyl groups, optionally substituted phenoxy groups, provided that at least one of $R_1$, $R_2$ or $R_3$ is an optionally substituted phenoxy group and, if $R_3$ is an optionally substituted phenoxy group, at least one of $R_1$ or $R_2$ is different from hydrogen;

$R_4$, which are the same as or different from each other, represent a hydrogen atom; or are selected from —COOR groups wherein R is selected from linear or branched $C_1$-$C_8$, preferably $C_1$-$C_4$, alkyl groups.

DETAILED DESCRIPTION OF THE DISCLOSURE

Figure 1:
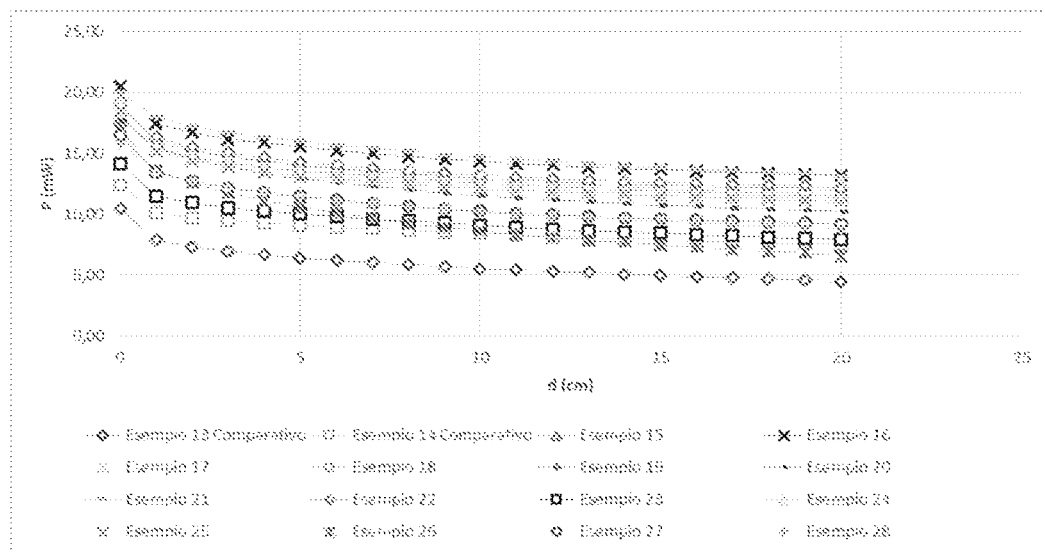
FIG. 1 depicts a plot showing a curve of power (P) generated as a function of the distance (d) from an edge to which the photovoltaic cell was fixed.

For the purposes of the present description and of the following claims, the definitions of numerical ranges will always include the extreme members, unless otherwise specified.

For the purposes of the present description and of the following claims, the term "comprising" will also include the terms "which essentially consists of" or "which consists of".

The term "$C_1$-$C_8$ alkyl groups" means linear or branched alkyl groups having from 1 to 8 carbon atoms. Specific examples of $C_1$-$C_8$ alkyl groups are: methyl, ethyl, n-propyl, iso-propyl, n-butyl, iso-butyl, t-butyl.

The term "optionally halogenated $C_1$-$C_8$ alkyl groups" means linear or branched, saturated or unsaturated alkyl groups having from 1 to 8 carbon atoms, wherein at least one of the hydrogen atoms is replaced by a halogen atom such as, for example, fluorine, chlorine, preferably fluorine. Specific examples of optional halogenated $C_1$-$C_8$ alkyl groups are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl.

The term "optionally substituted phenoxy groups" means $C_6H_5O$ phenoxy groups optionally substituted with one or more groups, which are the same as or different from each other, selected from: halogen atoms such as, for example, fluorine, chlorine, preferably fluorine; $C_1$-$C_{20}$ alkyl groups; $C_1$-$C_{20}$ alkoxy groups; cyano groups; amine groups; nitro groups; ester groups. Specific examples of $C_6H_5O$ phenoxy groups are: phenoxy, 4-octylphenoxy, 4-trifluoromethylphenoxy, 2-trifluoromethylphenoxy, 6-trifluoromethylphenoxy.

In accordance with a preferred embodiment of the present disclosure, in said general formula (I):

$R_1$, $R_2$ and $R_3$, which are the same as each other, are selected from optionally substituted phenoxy groups, preferably a phenoxy group; and $R_4$, which are the same as each other, represent a hydrogen atom; or $R_1$ and $R_3$, which are the same as each other, represent a hydrogen atom and $R_2$ is selected from optionally substituted phenoxy groups, preferably are a phenoxy group; and $R_4$, which are the same as each other, represent a hydrogen atom; or $R_1$ and $R_2$, which are the same as each other, are selected from optionally substituted phenoxy groups, are preferably a phenoxy group and $R_3$ represents a hydrogen atom; and $R_4$, which are the same as each other, represent a hydrogen atom; or $R_2$ and $R_3$, which are the same as each other, are selected from optionally substituted phenoxy groups, are preferably a phenoxy group and $R_1$ represents a hydrogen atom; and $R_4$, which are the same as each other, represent a hydrogen atom; or $R_1$ represents a hydrogen atom, $R_2$ is selected from $C_1$-$C_8$, preferably $C_1$-$C_4$, optionally halogenated linear or branched alkyl groups, preferably is methyl, and $R_3$ is selected from optionally substituted phenoxy groups, preferably is a phenoxy group; and $R_4$, which are the same as each other, represent a hydrogen atom; or $R_1$ is selected from $C_1$-$C_8$, preferably $C_1$-$C_4$, optionally halogenated linear or branched alkyl groups, preferably is trifluoromethyl, $R_2$ is selected from optionally substituted phenoxy groups, preferably is a phenoxy group, and $R_3$ represents a hydrogen atom; and $R_4$, which are the same as each other, represent a hydrogen atom; or $R_1$ and $R_3$, which are the same as each other, represent a hydrogen atom and $R_2$ is selected from optionally substituted phenoxy groups, preferably is a 4-trifluoromethylphenoxy group; and $R_4$, which are the same as each other, represent a hydrogen atom; or $R_1$ and $R_3$, which are the same as each other represent a hydrogen atom; $R_2$ is selected from optionally substituted phenoxy groups, preferably is a 2-trifluoromethylphenoxy group; and $R_4$, which are the same as each other, represent a hydrogen atom; or $R_1$ and $R_2$, which are the same as each other, are selected from optionally substituted phenoxy groups, preferably are a 4-octylphenoxy group and $R_3$ represents a hydrogen atom; and $R_4$, which are the same as each other, represent a hydrogen atom; or $R_1$ and $R_2$, which are the same as each other are selected from optionally substituted phenoxy groups, preferably are a 4-octylphenoxy group and $R_3$ represents a hydrogen atom; and $R_4$, which are the same as each other, are selected from —COOR groups wherein R is selected from $C_1$-$C_8$, preferably $C_1$-$C_4$, linear or branched alkyl groups, preferably represent a —COOCH$_3$ group; or $R_1$ and $R_3$, which are the same as each other, represent a hydrogen atom and $R_2$ is selected from optionally substituted phenoxy groups, preferably is a phenoxy group; and $R_4$, which are the same as each other, are selected from —COOR groups wherein R is selected from $C_1$-$C_8$, preferably $C_1$-$C_4$, linear or branched alkyl groups, preferably represent a —COOCH$_3$ group; or $R_1$, which are the same as each other, represent a halogen atom such as chlorine, bromine, fluorine, iodine, preferably represent a fluorine atom, $R_2$ is selected from optionally substituted phenoxy groups, preferably is a phenoxy group, and $R_3$, which are the same as each other, represent a hydrogen atom; and $R_4$, which are the same as each other, represent a hydrogen atom.

Specific examples of compounds having general formula (I) useful for the purpose of the present disclosure are given in Table 1.

TABLE 1
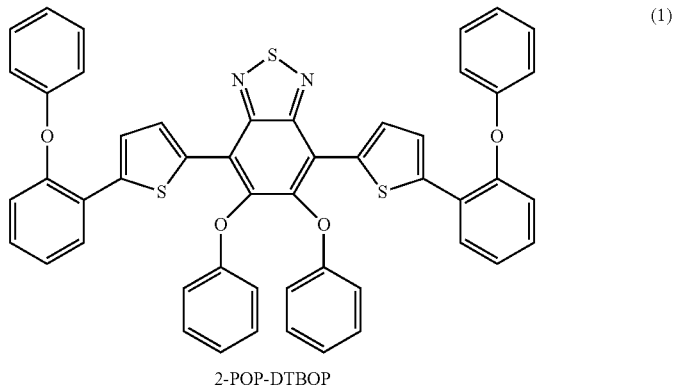
(1)
2-POP-DTBOP
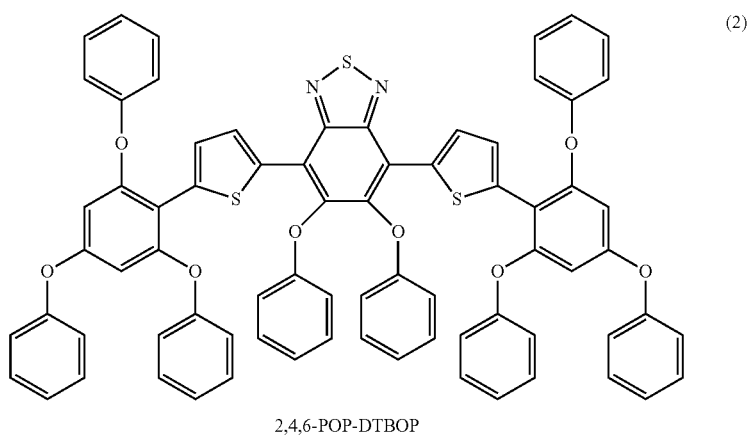
(2)
2,4,6-POP-DTBOP
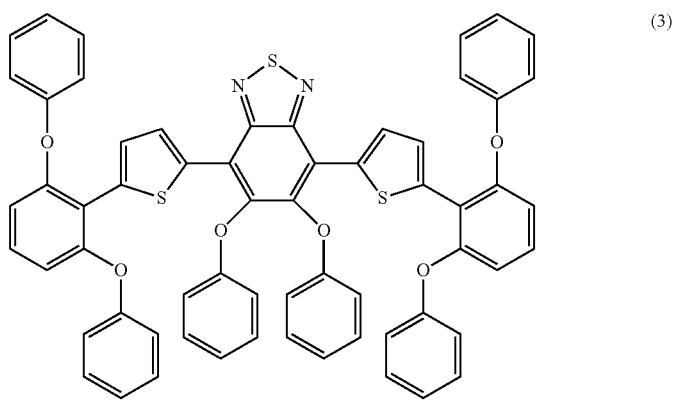
(3)
2,6-POP-DTBOP TABLE 1-continued
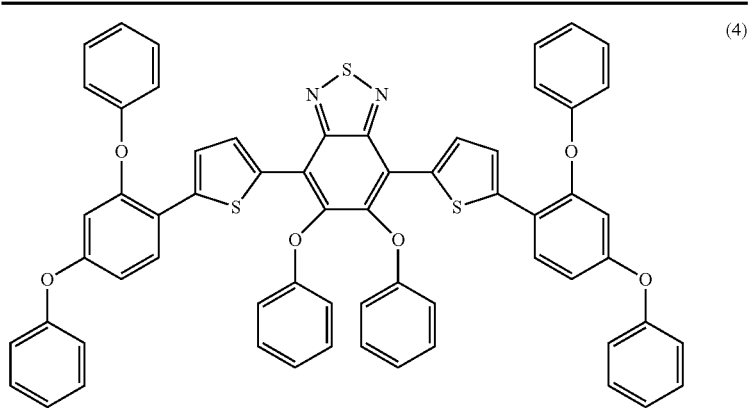
2,4-POP-DTBOP (4)
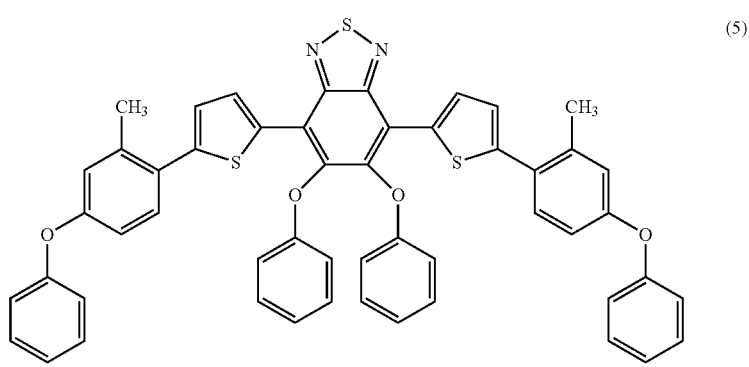
2-CH$_3$-4-POP-DTBOP (5)
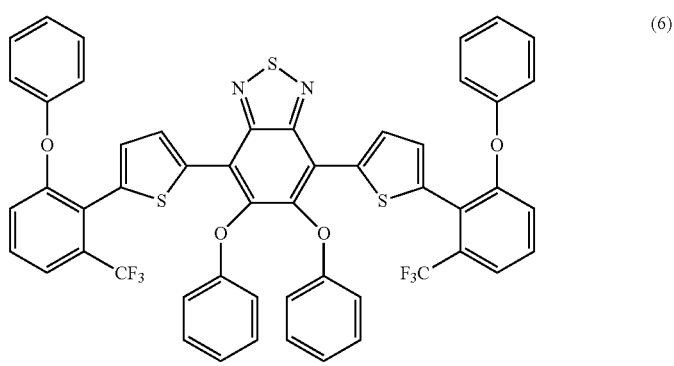
6-CF$_3$-2-POP-DTBOP (6)

TABLE 1-continued
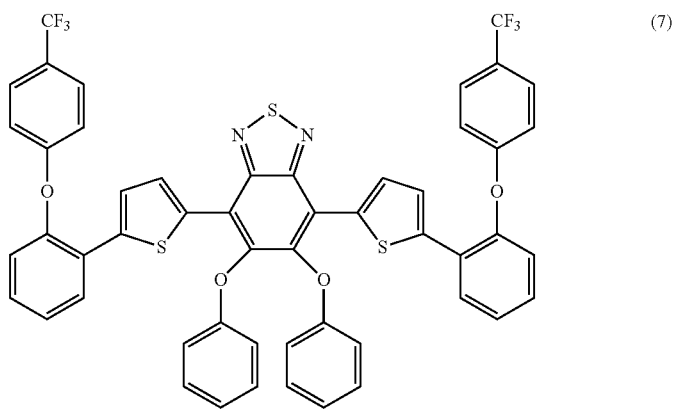
2-(POP-4-CF$_3$)-DTBOP (7)
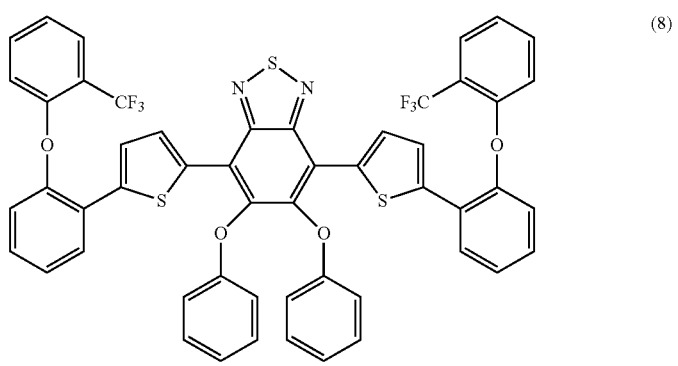
2-(POP-2-CF$_3$)-DTBOP (8)
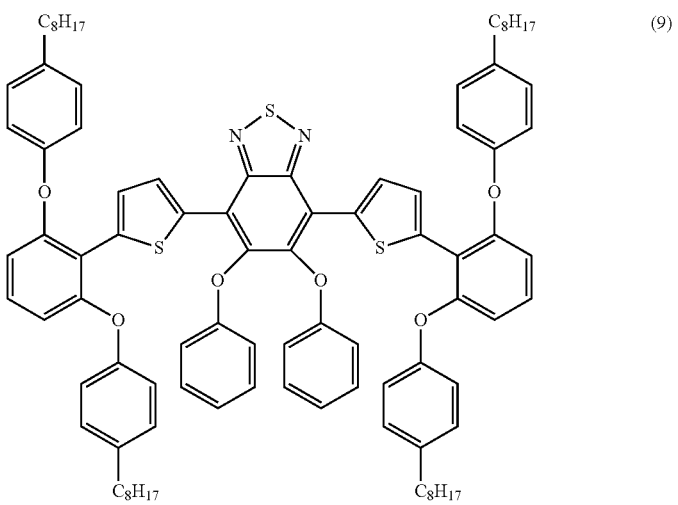
2,6-(POP-4-C$_8$H$_{17}$)-DTBOP (9)

TABLE 1-continued

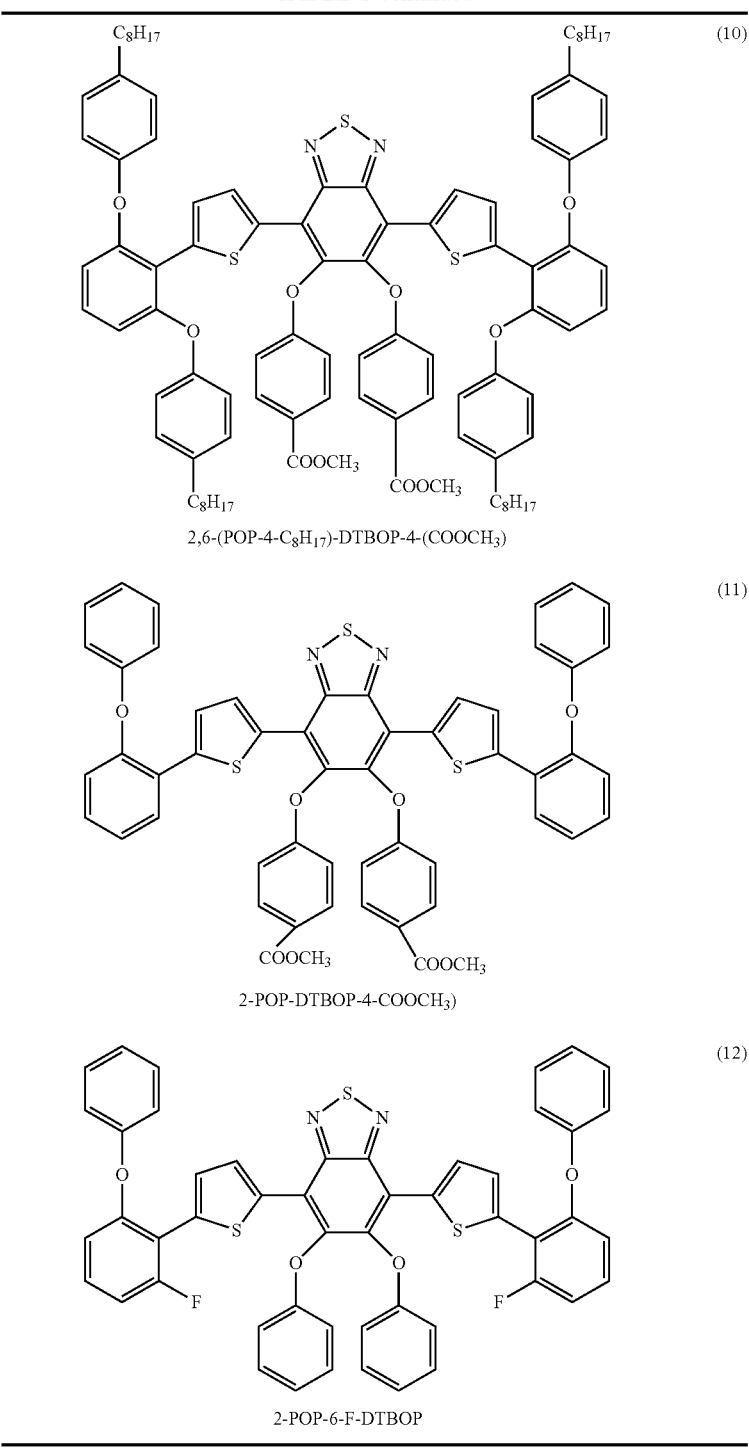

2,6-(POP-4-C8H17)-DTBOP-4-(COOCH3)   (10)

2-POP-DTBOP-4-COOCH3)   (11)

2-POP-6-F-DTBOP   (12)

The disubstituted diaryloxybenzoheterodiazole compound having general formula (I) which is the object of the present disclosure may be obtained by means of process known in the art by operating, for example, as described in the above-mentioned international patent application WO 2016/046319 or in Italian patent application MI201800000000667, both in the name of the Applicant and incorporated herein as a reference. Further details on the process for the preparation of said disubstituted diaryloxybenzoheterodiazole compound having general formula (I) may be found in the following examples.

As described above, said disubstituted diaryloxyheterodiazole compound having general formula (I) may advantageously be used as a spectrum converter in luminescent solar concentrators ("Luminescent Solar Concentrators"—LSCs) which, in turn, are capable of improving the performance of photovoltaic devices (or solar devices) such as, for example, photovoltaic cells (or solar cells), photovoltaic modules (or solar modules), on either a rigid or flexible support.

Said luminescent solar concentrators ("Luminescent Solar Concentrators"—LSCs) may be prepared, for example, by molten dispersion of said disubstituted diaryloxybenzoheterodiazole compound having general formula (I) in polymer materials such as, for example, polymethylmethacrylate (PMMA), polystyrene (PS), polyvinyl-acetate (PVA). Consequently, a further object of the present disclosure is a luminescent solar concentrator ("Luminescent Solar Concentrator"—LSC) including at least one disubstituted diaryloxybenzoheterodiazole compound having general formula (I).

The disubstituted diaryloxybenzoheterodiazole compound having general formula (I) may be used in said luminescent solar concentrator ("Luminescent Solar Concentrator"—LSC) in the following forms: dispersed in polymer or glass, chemically bonded to polymer or glass, in solution, or in gel form.

For example, the luminescent solar concentrator ("Luminescent Solar Concentrator"—LSC) may contain a transparent matrix, wherein the term transparent matrix means any transparent material used in the form of a support, binder, or material wherein at least one disubstituted diaryloxybenzoheterodiazole compound having general formula (I) is dispersed or incorporated. The material used for the matrix is, as such, transparent to the radiation of interest and in particular to radiation having a frequency included in the effective spectrum of the photovoltaic device (or solar device) such as, for example, the photovoltaic cell (or solar cell) wherein it is used. Materials suitable for the purpose of the present disclosure may therefore be selected from materials which are transparent to at least radiation having a wavelength ranging from 250 nm to 1100 nm.

The transparent matrix that may be used for the purpose of the present disclosure may be selected, for example, from polymer materials or glassy materials. Said matrix is characterized by high transparency and a long service life in terms of heat and light. Polymer materials that may advantageously be used for the purpose of the present disclosure are, for example, polymethylmethacrylate (PMMA), epoxy resins, silicone resins, polyalkylene terephthalates, polycarbonates, polystyrene, polypropylene. Glassy materials that may advantageously be used for the purpose of the present disclosure are, for example, silica.

In the case wherein the matrix is of polymer type, said at least one disubstituted diaryloxybenzoheterodiazole compound having general formula (I) may be dispersed in the polymer of said matrix by means, for example, of dispersion in molten form and subsequent formation of a sheet comprising said polymer and said at least one disubstituted diaryloxybenzoheterodiazole compound having general formula (I), operating, for example, according to the technique known as "casting". Alternatively, said at least one disubstituted diaryloxybenzoheterodiazole compound having general formula (I) and the polymer of said matrix may be solubilized in at least one solvent obtaining a solution that is deposited on a sheet of said polymer, forming a film including said at least one disubstituted diaryloxybenzoheterodiazole compound having general formula (I) and said polymer, operating, for example, through the use of a "Doctor Blade" type film applicator: said solvent is subsequently left to evaporate.

In the case wherein the matrix is of a glassy type, said at least one disubstituted diaryloxybenzoheterodiazole compound having general formula (I) may be solubilized in at least one solvent obtaining a solution that is deposited on a sheet of said glassy type matrix, forming a film including said at least one disubstituted diaryloxybenzoheterodiazole compound having general formula (I), operating, for example, through the use of a "Doctor Blade" type film applicator: said solvent is subsequently left to evaporate.

A photovoltaic device (or solar device) comprising at least one photovoltaic cell (or solar cell), and at least one luminescent solar concentrator ("Luminescent Solar Concentrator"—LSC) comprising at least one disubstituted, diaryloxybenzoheterodiazole compound having general formula (I) is also the object of the present disclosure.

Said photovoltaic device (or solar device) may be obtained, for example, by assembling the aforementioned luminescent solar concentrator with a photovoltaic cell (or solar cell).

According to a preferred embodiment of the present disclosure the above-mentioned solar concentrator may be constructed in the form of a transparent sheet obtained by the solubilization of said at least one disubstituted diaryloxybenzoheterodiazole compound having general formula (I) and the polymer of the polymer matrix in at least one solvent obtaining a solution that is deposited on a sheet of said polymer, forming a film comprising at least one disubstituted diaryloxybenzoheterodiazole compound having general formula (I) and said polymer, for example by using a "Doctor Blade" type film applicator: said solvent is subsequently left to evaporate. In said photovoltaic devices (or solar devices), said sheets may subsequently be coupled to a photovoltaic cell (or solar cell).

In order to better understand the present disclosure and to put it into practice some illustrative and non-limiting examples of it are described below.

EXAMPLES

The 4,7-di-(thien-2'-yl)-2,1,3-benzothiadiazole (DTB) was obtained as described in Example 1 of international patent application WO 2012/007834 in the name of the Applicant, the contents of which are incorporated herein as a reference.

Example 1 (Disclosure

Synthesis of 2-POP-DTBOP Having Formula (1)

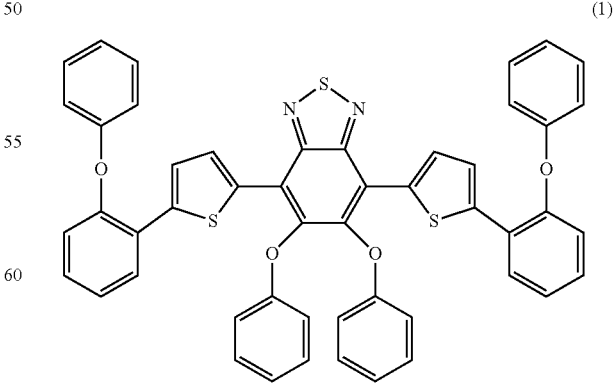

2-POP-DTBOP (1) Synthesis of 4,7-dibromo-5,6-diphenoxybenzothiadiazole Having Formula (a)

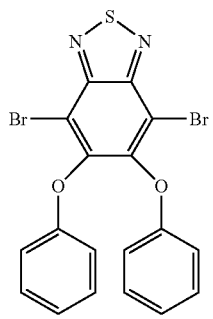

(a)

Phenol (Aldrich) (2.9 g; 2.8 ml; 31.6 mmol) and potassium carbonate (Aldrich) (4.4 g; 31.6 mmol) were added, under an inert atmosphere, to a 0.3 M solution of 4,7-dibromo-5,6-difluorobenzothiadiazole (Sunatech) (4.35 g; 13.2 mmol) in anhydrous N,N-dimethylformamide (Aldrich) (44 ml) in a 250 ml flask, equipped with a magnetic stirrer, thermometer and cooling system: the reaction mixture obtained was heated to 82'C and kept, at said temperature, under stirring, for 12 hours. Subsequently, after adding 100 ml of distilled water, a precipitate was obtained which was recovered by filtration, washed with distilled water (30 ml) and dried under vacuum, obtaining 6.3 g of 4,7-dibromo-5,6-diphenoxybenzothiadiazole having formula (a) (yield=100%).

(2) Synthesis of 4,7-dithienyl-5,6-diphenoxybenzothiadiazole Having Formula (b)

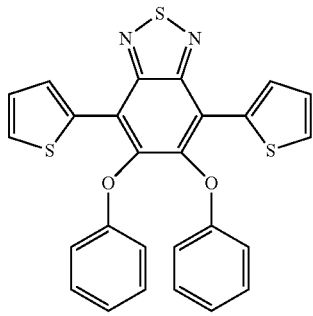

(b)

2-tributylstannylthiophene (Aldrich) (11.8 g; 10.1 ml; 31.7 mmol) was added, under an inert atmosphere, to a 0.1 M solution of 4,7-dibromo-5,6-diphenoxybenzothiadiazole having formula (a) obtained as described above (6.3 g; 13.2 mmol) in anhydrous toluene (Aldrich) (132 ml) in a 250 ml magnetically stirred flask, provided with a thermometer and cooling system. After the air present had been removed through 3 vacuum/nitrogen cycles, tris(dibenzylideneacetone) dipalladium (Aldrich) (0.352 g; 0.4 mmol) and tris-o-tolylphosphine (Aldrich) (0.441 g; 1.45 mmol) were added, obtaining a reaction mixture that was immersed in a bath preheated to 110° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 100 ml of methanol, obtaining a precipitate that was recovered by filtration and subsequently purified by elution on a silica gel chromatography column [graduated eluent: n-heptane (Aldrich)/dichloromethane (Aldrich) mixture, from ratio 9/1 (v/v) to ratio 8/2 (v/v) to ratio 6/4 (v(v)]. The product obtained was recrystallized from a mixture of n-heptane (Aldrich)/dichloromethane (Aldrich) (ratio 9/1 (v/v)) obtaining 5.7 g of 4,7-dithienyl-5,6-diphenoxybenzothiadiazole having formula (b) (yield=89%).

(3) Synthesis of 4,7-bis(5-bromo-2-thienyl)-5,6-diphenoxybenzothiadiazole Having Formula (c)

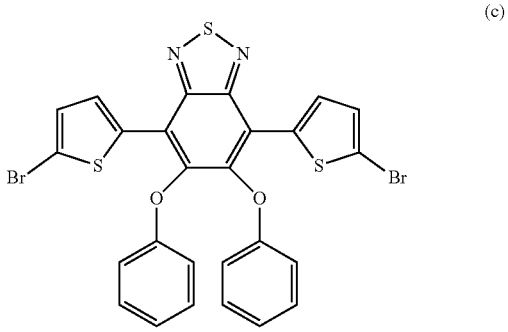

(c)

N-bromosuccinimide (Aldrich) (4.7 g; 26.3 mmol) was added, under an inert atmosphere, to a 0.05 M solution of 4,7-dithienyl-5,6-difluorobenzothiadiazole having formula (b) obtained as described above (5.7 g; 11.8 mmol) in anhydrous tetrahydrofuran (Aldrich) (230 ml) in a 500 ml magnetically stirred flask equipped with a thermometer and cooling system: the reaction mixture obtained was kept, under stirring, in the dark at room temperature (25'C), for 12 hours. Subsequently, after adding 200 ml of distilled water, a precipitate was obtained which was recovered by filtration, washed with methanol (Aldrich) (200 ml) and recrystallized from a mixture of n-heptane (Aldrich)/dichloromethane (Aldrich) [ratio 9/1 (v/v)] obtaining 7.4 g of 4,7-bis(5-bromo-2-thienyl)-5,6-diphenoxybenzothiadiazole having formula (c) (yield=98%).

(4) Synthesis of 2-POP-DTBOP (1)

2-phenoxyphenylboronic acid (Aldrich) (3.1 g; 14.7 mmol) and a 2.1 M aqueous solution of potassium carbonate (Aldrich) (6 g in 22 ml distilled water; 43.4 mmol) were added, under an inert atmosphere, to a 0.08 M solution of 4,7-bis(5-bromo-2-thienyl)-5,6-diphenoxybenzothiadiazole having formula (c) obtained as described above (3.5 g; 5.5 mmol) in anhydrous 1,4-dioxane (Aldrich) (66 ml) in a 250 ml flask equipped with a magnetic stirrer, thermometer and cooling system. After the air present had been removed through 3 vacuum/nitrogen cycles, tetrakis(phenyl)phosphine)palladium (Aldrich) (0.308 g; 0.27 mmol) was added, obtaining a reaction mixture that was immersed in a bath preheated to 85° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 100 ml of methanol, obtaining a precipitate that was recovered by filtration and subsequently purified by elution on a silica gel chromatography column [graduated eluent: n-heptane (Aldrich)/dichloromethane (Aldrich) mixture, from ratio 9/1 (v/v) to ratio 8/2 (v/v) to ratio 6/4 (v(v)]. The product obtained was recrystallized from a mixture of n-heptane (Aldrich)/dichloromethane (Aldrich) [ratio 9/1 (v/v)] obtaining 4.1 g of 2-POP-DTBOP having formula (1) (yield=90%).

Example 2 (Disclosure

Synthesis of 2-POP-6-F-DTBOP Having Formula (12)

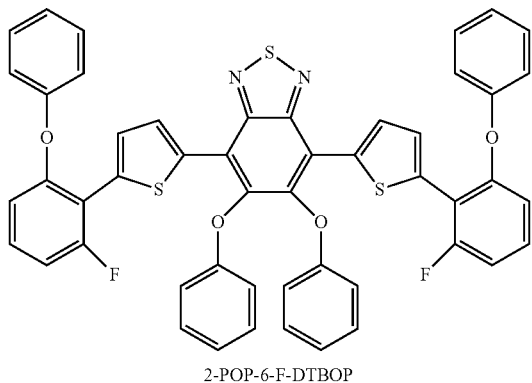 [SMILES: c1ccc(Oc2ccccc2-c2ccc(-c3c(Oc4ccccc4)c(Oc4ccccc4)c(-c4ccc(-c5ccccc5Oc5ccccc5)s4)c4nsnc34)s2)cc1]

2-POP-6-F-DTBOP (1) Synthesis of 2-phenoxy-6-fluoro-1-bromobenzene Having Formula (I'

The following were placed in a microwave vial: 2,4-difluoro-1-bromobenzene (Aldrich) (0.75 g; 3.9 mmol), phenol (0.365 g; 3.9 mmol), potassium carbonate (Aldrich) (1.5 g; 10.8 mmol) and N-methylpyrrolidone (Aldrich) (15 ml). After the reaction mixture obtained had been shaken, under a flow of argon, the vial was closed with its special cap and placed in a 50 ml reactor: the reaction ramp was set from 25° C. to 200° C. over 4 minutes. The reaction mixture was kept in the reactor at 200° C. for 40 minutes, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] obtaining 0.816 g of 2-phenoxy-6-fluoro-1-bromobenzene having formula (I') (yield=78%).

(2) Synthesis of 2-phenoxy-6-fluoro-1-(2-thienyl) benzene Having Formula (m'

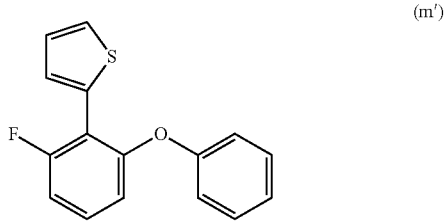

2-tributylstannylthiophene (Aldrich) (1.37 g; 1.14 ml; 3.67 mmol) was added, under an inert atmosphere, to a 0.1 M solution of 2-phenoxy-6-fluoro-1-bromobenzene having formula (I') obtained as described above (0.816 g; 3.06 mmol) in anhydrous toluene (Aldrich) (30.6 ml), in a 100 ml magnetically stirred flask equipped with a thermometer and cooling system. After the air present had been removed through 3 vacuum/nitrogen cycles, tris(dibenzylideneacetone)dipalladium (Aldrich) (0.042 g; 0.04 mmol) and tris-o-tolylphosphine (Aldrich) (0.051 g; 0.15 mmol) were added, obtaining a reaction mixture that was immersed in a bath preheated to 110° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After the residual solvent had been removed by reduced pressure distillation, the residue obtained was purified by elution on a silica gel chromatography column [eluent: n-heptane (Aldrich)] obtaining 0.8 g of 2-phenoxy-6-fluoro-1-(2-thienyl)benzene having formula (m') (yield=95%).

(3) Synthesis of 2-POP-6-F-DTBOP Having Formula (12)

n-Butyllithium (Aldrich) (1.6 M solution in hexane) (2 ml; 3.2 mmol) was added dropwise, under an inert atmosphere, to a 0.1 M solution of 2-phenoxy-6-fluoro-1-(2-thienyl)benzene having formula (m') obtained as described above (0.79 g; 2.9 mmol) in anhydrous tetrahydrofuran (Aldrich) (30 ml), at −78° C., in a 100 ml flask equipped with a magnetic stirrer and a thermometer: the reaction mixture obtained was kept under stirring and the temperature was raised to −50° C. over 3 hours. Subsequently, after the flask had been placed in a bath containing acetone and dry ice at −78° C., tributylstannylchloride (Aldrich) (1.14 g;

0.953 ml; 3.5 mmol) was added dropwise. After 15 minutes the flask was removed from the bath, the temperature was allowed to rise to 20° C. and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (1×25 ml) and subsequently dehydrated on sodium sulfate (Aldrich). After the residual solvent had been removed by reduced pressure distillation the residue obtained comprising 2-phenoxy-6-fluoro-1-[2' (5'-tributylstannyl)thienyl]benzene having formula (n'):

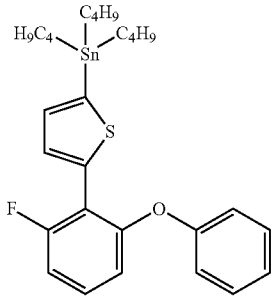

(n')

was used as follows.

In a 100 ml flask equipped with a magnetic stirrer, thermometer and cooling system, the residue comprising 2-phenoxy-6-fluoro-1-[2'(5'-tributylstannyl)thienyl]benzene having formula (n') obtained as described above, was dissolved in anhydrous toluene (Aldrich) (26 ml) obtaining a solution to which was added 4,7-dibromo-5,6-diphenoxy-benzothiadiazole having formula (a) obtained as described in Example 1 (0.48 g); 1 mmole), under an inert atmosphere. After the air present had been removed through 3 vacuum/nitrogen cycles, tris(dibenzylideneacetone)dipalladium (Aldrich) (0.03 g; 0.03 mmol) and tris-o-tolylphosphine (Aldrich) (0.04 g; 0.13 mmol) were added, obtaining a reaction mixture that was immersed in a bath preheated to 110'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloro-methane (Aldrich)/ethyl acetate (Aldrich) mixture 85/10/5 (v/v/v). The product obtained was recrystallized from a mixture of n-heptane (Aldrich)/dichloromethane (Aldrich) [ratio 9/1 (v/v)] obtaining 0.7 g of 2-POP-6-F-DTBOP having formula (12) (yield=80%).

Example 3 (Disclosure

Synthesis of 2-POP-(DTBOP-4-COOCH₃) Having Formula (11)

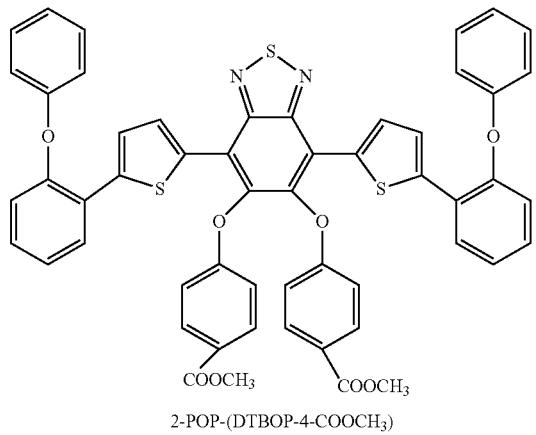 [SMILES: COC(=O)c1ccc(Oc2c(Oc3ccc(C(=O)OC)cc3)c(-c3ccc(-c4ccccc4Oc4ccccc4)s3)c3nsnc3c2-c2ccc(-c3ccccc3Oc3ccccc3)s2)cc1]

(11)

2-POP-(DTBOP-4-COOCH₃)

(1) Synthesis of 4,7-dibromo-5,6-di(4'-carbomethoxyphenoxy)benzothiadiazole Having Formula (d)

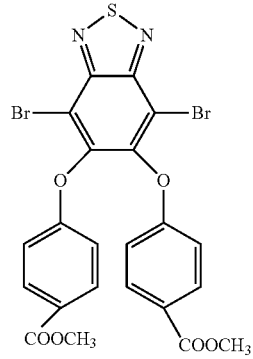

(d)

4-Carbomethoxyphenol (Aldrich) (1.1 g; 7.1 mmol) and potassium carbonate (Aldrich) (0.98 g; 7.1 mmol) were added, under an inert atmosphere, to a 0.3 M solution of 4,7-dibromo-5,6-difluorobenzothiadiazole (Sunatech) (1 g; 3 mmol) in anhydrous N,N-dimethylformamide (Aldrich) (15 ml) in a 250 ml flask equipped with a magnetic stirrer, thermometer and cooling system: the reaction mixture obtained was heated to 82'C and kept, at said temperature, under stirring, for 12 hours. Subsequently, after adding 100 ml of distilled water, a precipitate was obtained which was recovered by filtration, washed with distilled water (30 ml) and dried under vacuum, obtaining 1.75 g of 4,7-dibromo-5,6-di(4'-carbomethoxyphenoxy)benzothiadiazole having formula (d) (yield=98%).

(2) Synthesis of 4,7-dithienyl-5,6-di(4'-carbomethoxyphenoxy)benzothiadiazole Having Formula (e)

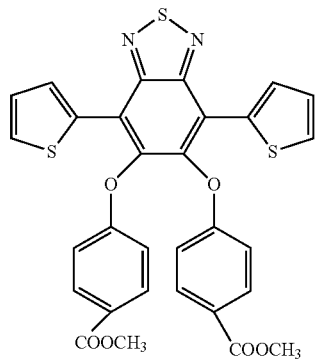

2-Tributylstannylthiophene (Aldrich) (1.5 g; 1.3 ml; 4.1 mmol) was added, under an inert atmosphere, to a 0.1 M solution of 4,7-dibromo-5,6-di(4'-carbomethoxyphenoxy)benzothiadiazole having formula (d) obtained as described above (1 g; 1.7 mmol) in anhydrous toluene (Aldrich) (17 ml) in a 100 ml flask equipped with a magnetic stirrer, thermometer and cooling system. After the air present had been removed through 3 vacuum/nitrogen cycles, tris(dibenzylideneacetone)dipalladium (Aldrich) (0.0454 g; 0.05 mmol) and tris-o-tolylphosphine (Aldrich) (0.0547 g; 0.18 mmol) were added, obtaining a reaction mixture that was immersed in a bath preheated to 110° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [graduated eluent: n-heptane (Aldrich)/dichloromethane (Aldrich) mixture from ratio 9/1 (v/v) to ratio 8/2 (v/v) to ratio 6/4 (v/v)]. The product obtained was recrystallized from a mixture of n-heptane (Aldrich)/dichloromethane (Aldrich) [ratio 9/1 (v/v)] to yield 0.9 g of 4,7-dithienyl-5,6-di(4'-carbomethoxyphenoxy)benzothiadiazole having formula (e) (yield=88%).

(3) Synthesis of 4,7-bis(5-bromo-2-thienyl)-5,6-di(4'-carbomethoxyphenoxy)-benzothiadiazole Having Formula (f)

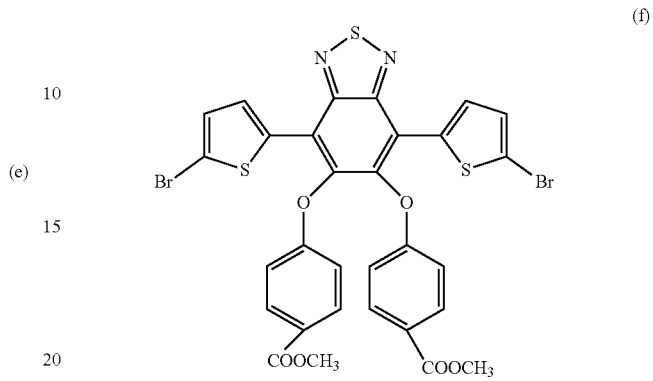

N-Bromosuccinimide (Aldrich) (0.592 g; 3.3 mmol) was added, under an inert atmosphere, to a 0.05 M solution of 4,7-dithienyl-5,6-di(4'-carbomethoxyphenoxy)-benzothiadiazole having formula (e) obtained as described above (0.9 g; 1.5 mmol) in anhydrous tetrahydrofuran (Aldrich) (30 ml) in a 100 ml flask equipped with a magnetic stirrer, thermometer and cooling system: the reaction mixture obtained was kept, under stirring, in the dark, at room temperature (25'C), for 12 hours. Subsequently, after adding 50 ml of distilled water, a precipitate was obtained which was recovered through filtration, washed with methanol (Aldrich) (200 ml) and recrystallized from a mixture of n-heptane (Aldrich)/dichloromethane (Aldrich) [ratio 9/1 (v/v)] to yield 1.1 g of 4,7-bis(5-bromo-2-thienyl)-5,6-di(4'-carbomethoxyphenoxy)-benzothiazole having formula (f) (yield=98%).

(4) Synthesis of 2-POP-(DTBOP-4-COOCH$_3$) Having Formula (11)

2-Phenoxyphenylboronic acid (Aldrich) (0.86 g; 4 mmol) and a 2 M aqueous solution of potassium carbonate (Aldrich) (1.66 g in 6 ml distilled water; 12 mmol) were added, under an inert atmosphere, to a 0.08 M solution of 4,7-bis(5-bromo-2-thienyl)-5,6-di(4'-carbomethoxyphenoxy)-benzothiadiazole having formula (f) obtained as described above (1.1 g; 5.5 mmol) in anhydrous 1,4-dioxane (Aldrich) (18 ml) in a 100 ml flask equipped with a magnetic stirrer, thermometer and cooling system. After the air present had been removed through 3 vacuum/nitrogen cycles, tetrakis(phenylphosphine)-palladium (Aldrich) (0.084 g; 0.07 mmol) was added, obtaining a reaction mixture that was immersed in a bath preheated to 85'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloro-methane (Aldrich)/ethyl acetate (Aldrich) mixture, ratio 8/1/1 (v/v/v)].

The product obtained was recrystallized from a mixture of n-heptane (Aldrich)/dichloro-methane (Aldrich) [ratio 9/1 (v/v)] obtaining 1.1 g of 2-POP-(DTBOP-4-COOCH₃) having formula (11) (yield=78%).

Example 4 (Disclosure

Synthesis of 2,6-POP-DTBOP Having Formula (3)

(3)

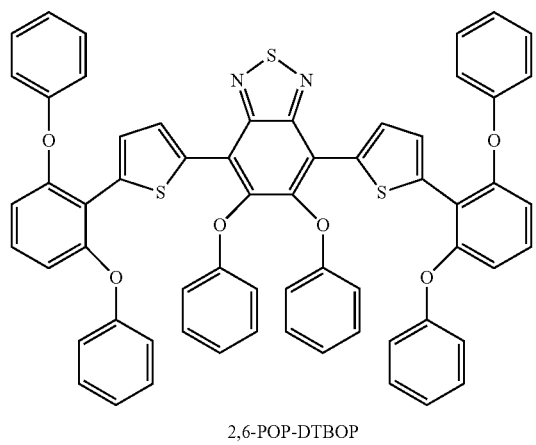

2,6-POP-DTBOP (1) Synthesis of 2,6-diphenoxy-1-bromobenzene Having Formula (g)

(g)

The following were placed in a microwave vial: 2,6-difluoro-1-bromobenzene (Aldrich) (0.85 g; 4.3 mmol), phenol (Aldrich) (1.9 g; 1.8 ml; 20 mmol), potassium carbonate (Aldrich) (2 g; 14.5 mmol) and N-methylpyrrolidone (Aldrich) (10 ml). After the reaction mixture obtained had been shaken under a flow of argon, the vial was closed with its special cap and placed in a 50 ml reactor: the reaction ramp was set from 25° C. to 210° C. over 4 minutes. The reaction mixture was kept in the reactor at 210° C. for 2 hours, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] obtaining 1.2 g of 2,6-diphenoxy-1-bromobenzene having formula (g) (yield=82%).

(2) Synthesis of 2,6-diphenoxy-1-(2-thienyl)benzene Having Formula (h)

(h)

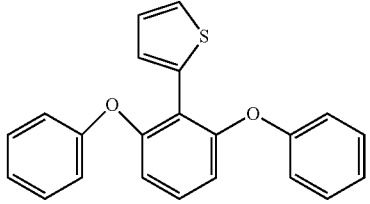

2-Tributylstannylthiophene (Aldrich) (1.3 g; 1.1 ml; 3.5 mmol) was added, under an inert atmosphere, to a 0.1 M solution of 2,6-diphenoxy-1-bromobenzene having formula (g) obtained as described above (1 g; 2.9 mmol) in anhydrous toluene (Aldrich) (29 ml) in a 100 ml flask equipped with a magnetic stirrer, thermometer and cooling system. After the air present had been removed through 3 vacuum/nitrogen cycles, tris(dibenzylidene-acetone)dipalladium (Aldrich) (0.04 g; 0.04 mmol) and tris-o-tolylphosphine (Aldrich) (0.046 g; 0.15 mmol) were added, obtaining a reaction mixture that was immersed in a bath preheated to 110'C and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] obtaining 0.95 g of 2,6-diphenoxy-1-(2-thienyl)benzene having formula (h) (yield=95%).

(3) Synthesis of 2,6-POP-DTBOP Having Formula (3)

n-Butyllithium (Aldrich) (1.6 M solution in hexane) (1.9 ml; 3 mmol) was added dropwise, under an inert atmosphere, to a 0.1 M solution of 2,6-diphenoxy-1-(2-thienyl)benzene having formula (h) obtained as described above (0.95 g; 2.7 mmol) in anhydrous tetrahydrofuran (Aldrich) (27 ml), at −78° C., in a 100 ml flask equipped with a magnetic stirrer and a thermometer: the reaction mixture obtained was kept under stirring and the temperature was raised to −50° C. in 3 hours. Subsequently, after the flask had been placed in a bath containing acetone and dry ice at −78° C., tributylstannylchloride (Aldrich) (1.1 g; 0.9 ml; 3.3 mmol) was added dropwise. After 15 minutes the flask was removed from the bath, the temperature was allowed to rise to 20'C and the reaction mixture was kept, at said temperature, under stirring, for 12 hours. Subsequently, after a saturated solution of sodium bicarbonate (Aldrich) (20 ml) had been added, the reaction mixture was extracted with ethyl ether (Aldrich) (20 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2,6-diphenoxy-1-[2'-(5'-tributylstannyl)thienyl]benzene having formula (i):

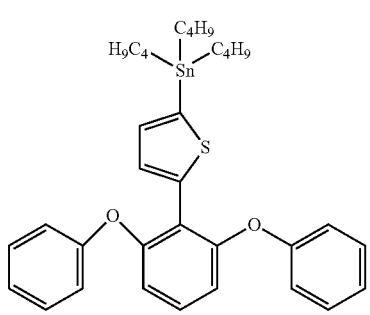

was used as follows.

The residue comprising 2,6-diphenoxy-1-[2'-(5'-tributyl-stannyl)thienyl]benzene having formula (i) obtained as described above was dissolved in anhydrous toluene (Aldrich) (25 ml) obtaining a solution to which was added, under an inert atmosphere, 4,7-dibromo-5,6-diphenoxyben-zothiadiazole having formula (a) obtained as described in Example 1 (0.6 g; 1.25 mmoles) in a 100 ml flask equipped with a magnetic stirrer and thermometer. After the air present had been removed through 3 vacuum/nitrogen cycles, tris(dibenzylidene-acetone)dipalladium (Aldrich) (0.034 g; 0.04 mmol) and tris-o-tolylphosphine (Aldrich) (0.043 g; 0.14 mmol) were added, obtaining a reaction mixture that was immersed in a bath preheated to 110'C and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture ratio 9/1 (v/v)]. The product obtained was recrystallized from a mixture of n-heptane (Aldrich)/dichloromethane (Aldrich) [ratio 9/1 (v/v)] obtaining 1 g of 2,6-POP-DTBOP having formula (3) (yield=80%).

Example 5 (Disclosure

Synthesis of 2,4-POP-DTBOP Having Formula (4)

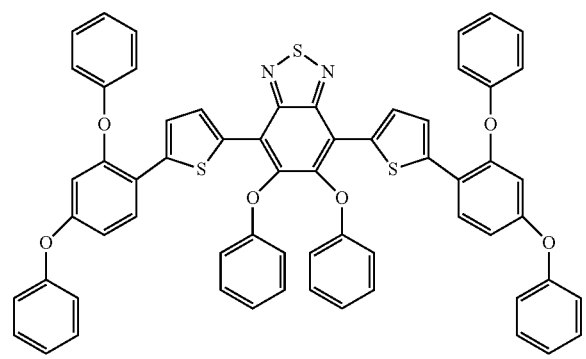

2,4-POP-DTBOP (1) Synthesis of 2,4-diphenoxy-1-bromobenzene Having Formula (I)

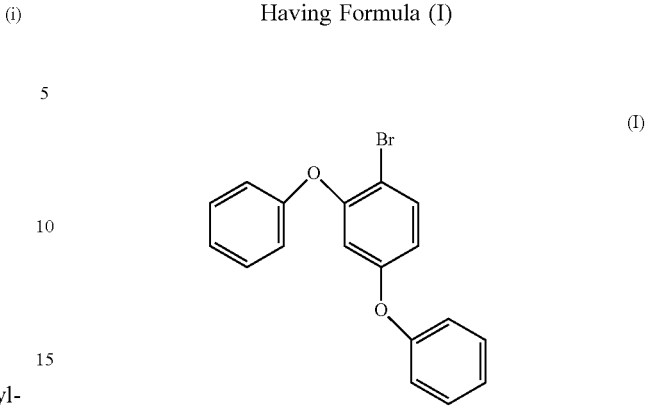

The following were placed in a microwave vial: 2,4-difluoro-1-bromobenzene (Aldrich) (2 g; 10.4 mmol), phenol (Aldrich) (3.2 g; 3 ml; 34.1 mmol), potassium carbonate (Aldrich) (5.7 g; 41.3 mmol) and N-methylpyrrolidone (Aldrich) (26 ml). After the reaction mixture obtained had been shaken under a flow of argon, the vial was closed with its special cap and placed in a 50 ml reactor: the reaction ramp was set from 25° C. to 220° C. over 4 minutes. The reaction mixture was kept in the reactor at 220° C. for 1 hour, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] to obtain 3.4 g of 2,4-diphenoxy-1-bromobenzene having formula (I) (yield=96%).

(2) Synthesis of 2,4-diphenoxy-1-(2-thienyl)benzene Having Formula (m)

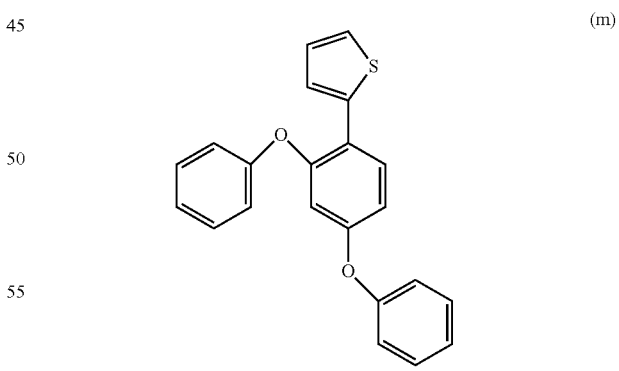

2-Tributylstannylthiophene (Aldrich) (1.2 g; 1 ml; 3.2 mmol) was added, under an inert atmosphere, to a 0.1 M solution of 2,4-diphenoxy-1-bromobenzene having formula (I) obtained as described above (0.91 g; 3.2 mmol) in anhydrous toluene (Aldrich) (27 ml) in a 100 ml flask equipped with a magnetic stirrer and thermometer. After the air present had been removed by 3 vacuum/nitrogen cycles, tris(dibenzylideneacetone)dipalladium (Aldrich) (0.0364 g;

0.04 mmol) and tris-o-tolylphosphine (Aldrich) (0.0462 g; 0.15 mmol) were added, obtaining a reaction mixture that was immersed in a bath preheated to 110° C. and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] to obtain 0.88 g of 2,4-diphenoxy-1-(2-thienyl)-benzene having formula (m) (yield=95%).

(3) Synthesis of 2,4-POP-DTBOP Having Formula (4)

n-Butyllithium (Aldrich) (1.6 M solution in hexane) (1.7 ml; 2.7 mmol) was added dropwise, under an inert atmosphere, to a 0.1 M solution of 2,4-diphenoxy-1-(2-thienyl) benzene having formula (m) obtained as described above (0.87 g; 2.5 mmol) in anhydrous tetrahydrofuran (Aldrich) (25 ml) at −78° C. in a 100 ml flask equipped with a magnetic stirrer and a thermometer: the reaction mixture obtained was kept under stirring and the temperature was raised to −50° C. over 3 hours. After the flask had been placed in a bath containing acetone and dry ice at −78° C., tributylstannylchloride (Aldrich) (0.98 g; 0.8 ml; 3 mmol) was added dropwise. After 15 minutes the flask was removed from the bath, the temperature was allowed to rise to 20'C and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (20 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2,4-phenoxy-1-[2'(5'-tributylstannyl) thienyl]benzene having formula (n):

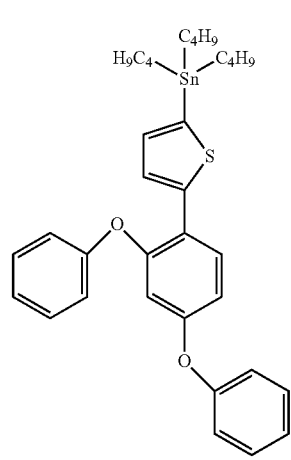

(n)

was used as follows.

The residue comprising 2,4-diphenoxy-1-[2'(5'-tributyl-stannyl)thienyl]benzene having formula (n) obtained as described above was dissolved in anhydrous toluene (Aldrich) (25 ml) in a 100 ml flask equipped with a magnetic stirrer and a thermometer and a cooling system, under an inert atmosphere, and to this was added 4,7-dibromo-5,6-diphenoxybenzothiadiazole having formula (a) obtained as described in Example 1 (0.5 g; 1.04 mmoles). After the air present had been removed through 3 vacuum/nitrogen cycles, tris(dibenzylideneacetone)dipalladium (Aldrich) (0.03 g; 0.03 mmol) and tris-o-tolylphosphine (Aldrich) (0.04 g; 0.13 mmol) were added, obtaining a reaction mixture that was immersed in a bath preheated to 110° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture ratio 9/1 (v/v)]. The product obtained was recrystallized from a mixture of n-heptane (Aldrich)/dichloromethane (Aldrich) [ratio 9/1 (v/v)] obtaining 0.83 g of 2,4-POP-DTBOP having formula (4) (yield=80%).

Example 6 (Disclosure

Synthesis of 2,4,6-POP-DTBOP Having Formula (2)

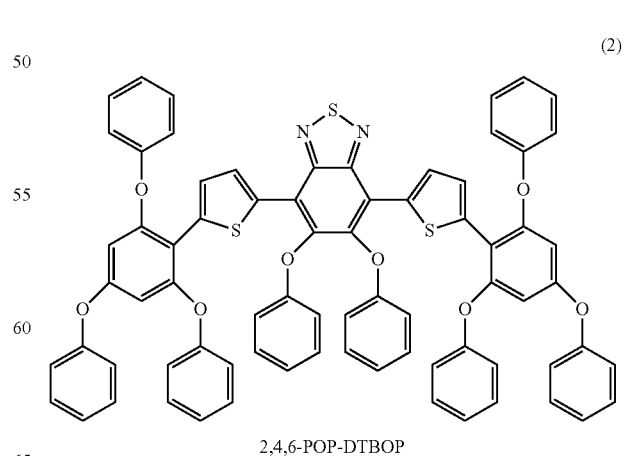

2,4,6-POP-DTBOP (2)

(1) Synthesis of 2,4,6-triphenoxy-1-bromobenzene Having Formula (o)

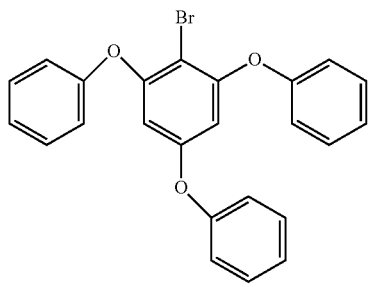

The following were placed in a microwave vial: 2,4,6-trifluoro-1-bromobenzene (Aldrich) (1.6 g; 0.9 mmol), phenol (Aldrich) (3.4 g; 3.2 ml; 36.2 mmol), potassium carbonate (Aldrich) (5 g; 36.2 mmol) and N-methylpyrrolidone (Aldrich) (26 ml). After the reaction mixture obtained had been shaken under a flow of argon, the vial was closed with its special cap and placed in a 50 ml reactor: the reaction ramp was set from 25° C. to 220° C. over 4 minutes. The reaction mixture was kept in the reactor at 220° C. for 3 hours, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] obtaining 2.3 g of 2,4,6-triphenoxy-1-bromobenzene having formula (o) (yield=70%).

(2) Synthesis of 2,4,6-triphenoxy-1-(2-thienyl)benzene Having Formula (p)

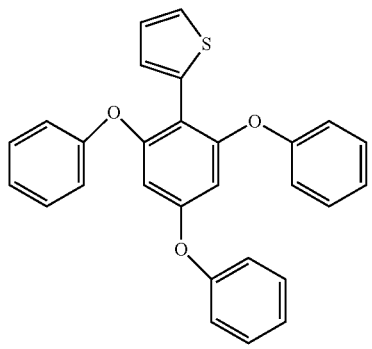

2-Tributylstannylthiophene (Aldrich) (1.5 g; 1.3 ml; 4.2 mmol) was added, under an inert atmosphere, to a 0.1 M solution of 2,4,6-triphenoxy-1-bromobenzene having formula (o) obtained as described above (1.5 g; 3.5 mmol) in anhydrous toluene (Aldrich) (35 ml) in a 100 ml flask equipped with a magnetic stirrer, thermometer and cooling system. After the air present had been removed through 3 vacuum/nitrogen cycles, tris(dibenzylidene-acetone)dipalladium (Aldrich) (0.048 g; 0.05 mmol) and tris-o-tolylphosphine (Aldrich) (0.06 g; 0.19 mmol) were added, obtaining a reaction mixture that was immersed in a bath preheated to 110'C and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] obtaining 1.1 g of 2,4,6-triphenoxy-1-(2-thienyl)benzene having formula (p) (yield=72%).

(4) Synthesis of 2,4,6-POP-DTBOP Having Formula (2)

n-Butyllithium (Aldrich) (1.6 M solution in hexane) (0.8 ml; 1.3 mmol) was added dropwise, under an inert atmosphere, to a 0.1 M solution of 2,4,6-triphenoxy-1-(2-thienyl)benzene having formula (p) obtained as described above (0.5 g; 1.15 mmol), in anhydrous tetrahydrofuran (Aldrich) (11 ml), at −78° C., in a 100 ml flask equipped with a magnetic stirrer and a thermometer: the reaction mixture obtained was kept under stirring and the temperature was raised to −50° C. over 3 hours. Afterwards, after the flask had been placed in a bath containing acetone and dry ice at −78° C., tributylstannylchloride (Aldrich) (0.5 g; 0.4 ml; 1.4 mmol) was added dropwise: after 15 minutes the flask was removed from the bath, the temperature was allowed to rise to 20'C and the reaction mixture was kept, at said temperature, under stirring, for 12 hours. Subsequently, after a saturated solution of sodium bicarbonate had been added (Aldrich) (30 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2,4,6-triphenoxy-1-[2'(5'-tributylstannyl)thienyl]benzene having formula (q):

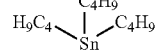
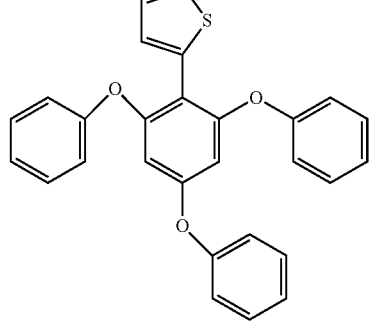

was used as follows.

The residue comprising 2,4,6-triphenoxy-1-[2'(5'-tributylstannyl)thienyl]benzene having formula (q) obtained as described above was dissolved in anhydrous toluene (Aldrich) (11.5 ml) in a 100 ml flask equipped with a magnetic stirrer, thermometer and cooling system, under an inert atmosphere, and to this was added 4,7-dibromo-5,6-diphenoxybenzothiadiazole having formula (a) obtained as described in Example 1 (0.24 g; 0.5 mmoles). After the air present had been removed through 3 vacuum/nitrogen cycles, tris(dibenzylideneacetone)dipalladium (Aldrich) (0.0136 g; 0.015 mmol) and tris-o-tolylphosphine (Aldrich) (0.0182 g; 0.06 mmol) were added, obtaining a reaction mixture that was immersed in a bath preheated to 110'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture ratio 9/1 (v/v)]. The product obtained was recrystallized from a mixture of n-heptane (Aldrich)/dichloromethane (Aldrich) [ratio 9/1 (v/v)] obtaining 0.44 g of 2,4,6-POP-DTBOP having formula (2) (yield=75%).

Example 7 (Disclosure

Synthesis of 2-CH$_3$-4-POP-DTBOP Having Formula (5)

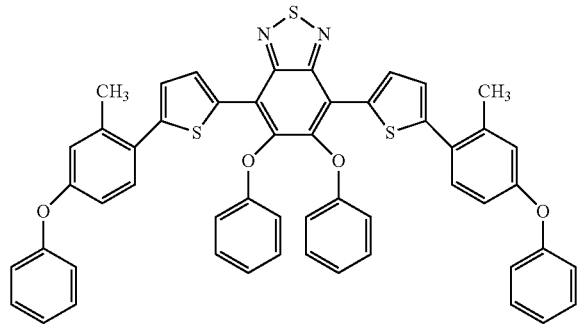

2-CH$_3$-4-POP-DTBOP (1) Synthesis of 2-methyl-4-phenoxy-1-bromobenzene Having Formula (r)

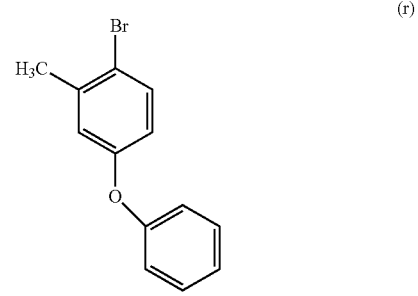

The following were placed in a microwave vial: 2-methyl-4-fluoro-1-bromobenzene (Aldrich) (1 g; 5.3 mmoles), phenol (Aldrich) (2.1 g; 2 ml; 22.8 mmoles), potassium carbonate (Aldrich) (1.4 g; 10.1 mmoles) and N-methylpyrrolidone (Aldrich) (12 ml). After the reaction mixture obtained had been shaken under a flow of argon, the vial was closed with its special cap and placed in a 50 ml reactor: the reaction ramp was set from 25° C. to 220° C. over 4 minutes. The reaction mixture was kept in the reactor at 220° C. for 3 hours, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] obtaining 0.7 g of 2-methyl-4-phenoxy-1-bromobenzene having formula (r) (yield=51%).

(2) Synthesis of 2-methyl-4-phenoxy-1-(2'-thienyl) benzene Having Formula (s)

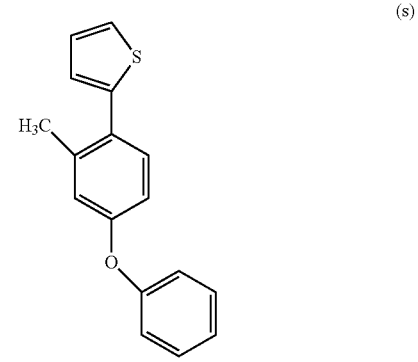 [SMILES: Cc1cc(Oc2ccccc2)ccc1-c1cccs1]

2-Tributylstannylthiophene (Aldrich) (1 g; 0.9 ml; 3.2 mmol) was added, under an inert atmosphere, to a 0.2 M solution of 2-methyl-4-phenoxy-1-bromobenzene having formula (r) obtained as described above (0.7 g; 2.7 mmol) in anhydrous toluene (Aldrich) (13 ml) in a 100 ml flask equipped with a magnetic stirrer and thermometer. After the air present had been removed by 3 vacuum/nitrogen cycles, tris(dibenzylideneacetone)dipalladium (Aldrich) (0.0364 g;

0.04 mmol) and tris-o-tolylphosphine (Aldrich) (0.0462 g; 0.15 mmol) were added, obtaining a reaction mixture that was immersed in a bath preheated to 110° C. and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 30 ml of methanol, obtaining a precipitate that was recovered by filtration and subsequently purified by elution on a silica gel chromatography column [eluent: n-heptane (Aldrich)] obtaining 1.1 g of 2-methyl-4-phenoxy-1-(2'-thienyl)-benzene having formula (s) (yield=98%).

(3) Synthesis of 2-CH$_3$-4-POP-DTBOP Having Formula (5)

n-Butyllithium (Aldrich) (1.6 M solution in hexane) (1.9 ml; 3 mmol) was added, under an inert atmosphere, to a 0.1 M solution of 2-methyl-4-phenoxy-1-(2'-thienyl)benzene having formula (s) obtained as described above (0.7 g; 2.7 mmol) in anhydrous tetrahydrofuran (Aldrich) (27 ml) dropwise at −78° C. in a 100 ml flask equipped with a magnetic stirrer and a thermometer: the reaction mixture obtained was kept under stirring and the temperature was raised to −50° C. over 3 hours. Subsequently, after the flask had been placed in a bath containing acetone and dry ice at −78° C., tributylstannylchloride (Aldrich) (0.5 g; 0.4 ml; 1.4 mmol) was added dropwise. After 15 minutes the flask was removed from the bath, the temperature was allowed to rise to 20'C and the reaction mixture was kept, at said temperature, under stirring, for 12 hours. Subsequently, after a saturated solution of sodium bicarbonate had been added (Aldrich) (30 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2-methyl-4-phenoxy-1-[2'(5'-tributylstannyl)thienyl] benzene having formula (t):

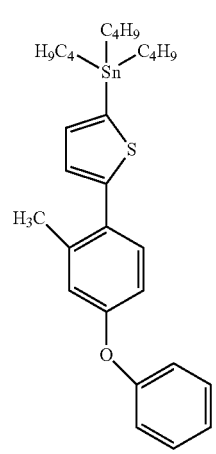

(t)

was used as follows.

In a 100 ml flask equipped with a magnetic stirrer, thermometer and cooling system, under an inert atmosphere, the residue comprising 2-methyl-4-phenoxy-1-[2'(5'-tributylstannyl)thienyl]benzene having formula (t) obtained as described above was dissolved in anhydrous toluene (Aldrich) (27 ml) to which was added 4,7-dibromo-5,6-diphenoxybenzothiadiazole having formula (a) obtained as described in Example 1 (0.525 g; 1.1 mmoles). After the air present had been removed through 3 vacuum/nitrogen cycles, tris(dibenzylideneacetone)dipalladium (Aldrich) (0.03 g; 0.033 mmol) and tris-o-tolylphosphine (Aldrich) (0.04 g; 0.13 mmol) were added, obtaining a reaction mixture that was immersed in a bath preheated to 110'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture, ratio 9/1 (v/v)]. The product obtained was recrystallized from a mixture of n-heptane (Aldrich)/dichloromethane (Aldrich) [ratio 9/1 (v/v)] obtaining 0.74 g of 2-CH$_3$—POP-DTBOP having formula (5) (yield=80%).

Example 8 (Disclosure

Synthesis of 6-CF$_3$-2-POP-DTBOP Having Formula (6)

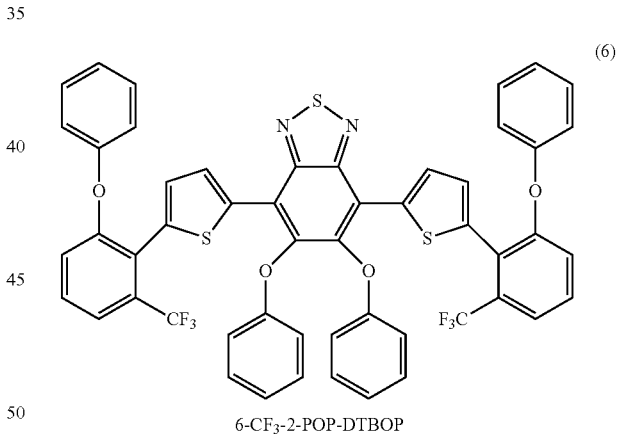

6-CF$_3$-2-POP-DTBOP (1) Synthesis of 6-trifluoromethyl-2-phenoxy-1-bromobenzene Having Formula (u)

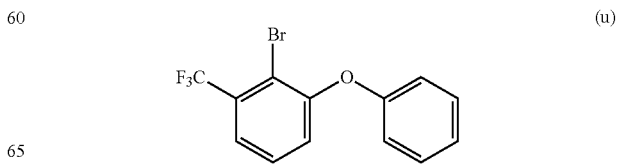

(u)

The following were placed in a microwave vial: 6-trifluoromethyl-2-fluoro-1-bromobenzene (Aldrich) (1 g; 4.1 mmol), phenol (Aldrich) (0.8 g; 0.7 ml; 8.2 mmol), potassium carbonate (Aldrich) (1.1 g; 8.2 mmol) and dimethylformamide (Aldrich) (20 ml). After the reaction mixture obtained had been shaken under a flow of argon, the vial was closed with its special cap and placed in a 50 ml reactor: the reaction ramp was set from 25° C. to 150° C. over 4 minutes. The reaction mixture was kept in the reactor at 150° C. for 45 minutes, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] to obtain 1 g of 6-trifluoromethyl-2-phenoxy-1-bromobenzene formula (u) (yield=77%).

(2) Synthesis of 6-trifluoromethyl-2-phenoxy-1-(2'-thienyl)benzene Having Formula (v)

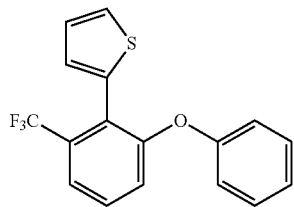

(v)

2-Tributylstannylthiophene (Aldrich) (1.4 g; 1.2 ml; 3.8 mmol) was added, under an inert atmosphere, to a 0.2 M solution of 6-trifluoromethyl-2-phenoxy-1-bromobenzene having formula (u) obtained as described above (1 g; 3.1 mmol) in anhydrous toluene (Aldrich) (21 ml) in a 100 ml flask equipped with a magnetic stirrer, thermometer and cooling system. After the air present had been removed through 3 vacuum/nitrogen cycles, tris(dibenzylideneacetone)dipalladium (Aldrich) (0.0435 g; 0.05 mmol) and tris-o-tolylphosphine (Aldrich) (0.0535 g; 0.18 mmol) were added, obtaining a reaction mixture that was immersed in a bath preheated to 110'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] to obtain 0.7 g of 6-trifluoromethyl-2-phenoxy-1-(2'-thienyl)benzene having formula (v) (yield=71%).

(3) Synthesis of 6-CF₃-2-POP-DTBOP Having Formula (6)

n-Butyllithium (Aldrich) (1.6 M solution in hexane) (1.5 ml; 2.4 mmol) was added dropwise, under an inert atmosphere, to a 0.1 M solution of 6-trifluoromethyl-2-phenoxy-1-(2'-thienyl)benzene having formula (v) obtained as described above (0.7 g; 2.2 mmol) in anhydrous tetrahydrofuran (Aldrich) (22 ml), at −78° C., in a 100 ml flask equipped with a magnetic stirrer, thermometer and cooling system: the reaction mixture obtained was kept under stirring and the temperature was raised to −50'C over 3 hours. Subsequently, after the flask had been placed in a bath containing acetone and dry ice at −78° C., tributylstannylchloride (Aldrich) (0.9 g; 0.7 ml; 2.6 mmol) was added dropwise. After 15 minutes the flask was removed from the bath, the temperature was allowed to rise to 20'C and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 6-trifluoromethyl-2-phenoxy-1-[2'(5'-tributylstannyl)thienyl]benzene having formula (z):

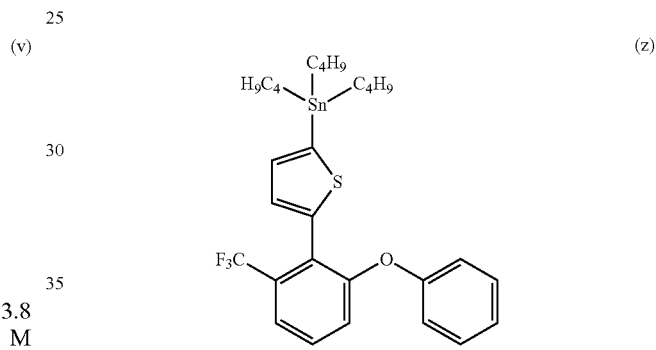

(z)

was used as follows.

In a 100 ml flask equipped with a magnetic stirrer, thermometer and cooling system, under an inert atmosphere, the residue comprising 6-trifluoromethyl-2-phenoxy-1-[2' (5'-tributylstannyl)thienyl)]benzene having formula (z) obtained as described above, was dissolved in anhydrous toluene (Aldrich) (22 ml) obtaining a solution to which was added 4,7-dibromo-5,6-diphenoxybenzothiadiazole having formula (a) obtained as described in Example 1 (0.449 g; 0.9 mmoles). After the air present had been removed through 3 vacuum/nitrogen cycles, tris(dibenzylideneacetone)dipalladium (Aldrich) (0.027 g; 0.03 mmol) and tris-o-tolylphosphine (Aldrich) (0.034 g; 0.11 mmol) were added, obtaining a reaction mixture that was immersed in a bath preheated to 110° C. and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture, ratio 9/1 (v/v)]. The product obtained was recrystallized from a mixture of n-heptane (Aldrich)/dichloromethane (Aldrich) [ratio 9/1 (v/v)] obtaining 0.6 g of 6-CF3-2-POP-DTBOP having formula (6) (yield=70%).

Example 9 (Disclosure

Synthesis of 2-(POP-4-CF$_3$)-DTBOP Having Formula (7)

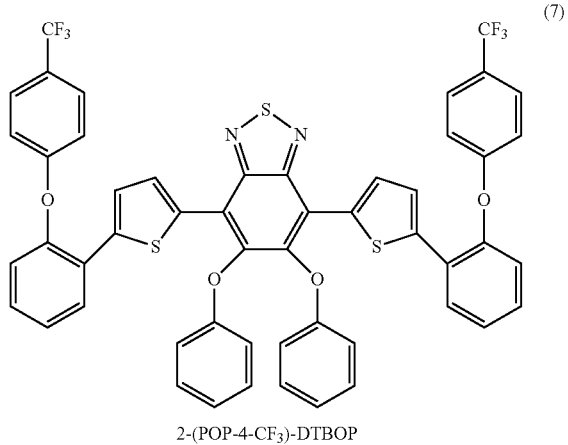 [SMILES: FC(F)(F)c1ccc(Oc2ccccc2-c2ccc(-c3c(Oc4ccccc4)c(Oc4ccccc4)c(-c4ccc(-c5ccccc5Oc5ccc(C(F)(F)F)cc5)s4)c4nsnc34)s2)cc1]

2-(POP-4-CF3)-DTBOP (1) Synthesis of 2-(4'-trifluoromethylphenoxy)-1-bromobenzene Having Formula (a'

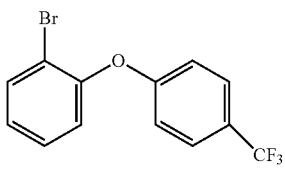

The following were placed in a microwave vial: 2-bromophenol (Aldrich) (0.57 g; 0.38 ml; 3.3 mmol), 4-fluoro-1-trifluoromethylbenzene (Aldrich) (0.54 g; 0.42 ml; 3.3 mmol), potassium carbonate (Aldrich) (0.5 g; 3.6 mmol) and dimethylformamide (Aldrich) (5 ml). After the reaction mixture obtained had been shaken under a flow of argon the vial was closed with its special cap and placed in a 50 ml reactor: the reaction ramp was set from 25° C. to 190° C. over 4 minutes. The reaction mixture was kept in the reactor at 190° C. for 45 minutes, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] obtaining 0.5 g of 2-(4'-trifluoromethylphenoxy)-1-bromobenzene having formula (a') (yield=50%).

(2) Synthesis of 2-(4'-trifluoromethylphenoxy)-1-(2'-thienyl)benzene Having Formula (b'

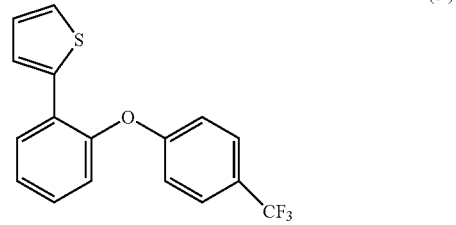

2-Thienylboronic acid (Aldrich) (0.33 g; 2.6 mmol) and a 2 M aqueous solution of potassium carbonate (Aldrich) (1.18 g in 4.3 ml distilled water; 8.6 mmol) were added, under an inert atmosphere, to a 0.2 M solution of 2-(4-trifluoromethylphenoxy)-1-bromobenzene having formula (a') obtained as described above (0.67 g.; 2.1 mmol) in anhydrous 1,4-dioxane (Aldrich) (16 ml) in a 100 ml flask equipped with a magnetic stirrer, thermometer and cooling system. After the air present had been removed through 3 vacuum/nitrogen cycles, tetrakis(triphenylphosphine)palladium (Aldrich) (0.05 g; 0.04 mmol) was added, obtaining a reaction mixture that was immersed in a bath preheated to 85'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by distillation at reduced pressure, the residue obtained was added dropwise to 50 ml of methanol, obtaining a precipitate that was recovered by filtration and subsequently purified by elution on a silica gel chromatography column [eluent: n-heptane (Aldrich)] to obtain 0.35 g of 2-(4'-trifluoromethylphenoxy)-1-(2'-thienyl)benzene having formula (b') (yield=52%).

(3) Synthesis of 2-(POP-4-CF$_3$)-DTBOP Having Formula (7)

n-Butyllithium (Aldrich) (1.6 M solution in hexane) (0.75 ml; 1.2 mmol) was added dropwise, under an inert atmosphere, to a 0.1 M solution of 2-(4-trifluoromethylphenoxy)-1-(2'-thienyl)benzene having formula (b') obtained as described above (0.35 g; 1.1 mmol) in anhydrous tetrahydrofuran (Aldrich) (10 ml), at −78° C., in a 100 ml flask equipped with a magnetic stirrer and a thermometer: the reaction mixture obtained was kept under stirring and the temperature was raised to −50'C over 3 hours. After the flask had been placed in a bath containing acetone and dry ice at −78° C., tributylstannylchloride (Aldrich) (0.43 g; 0.4 ml; 1.3 mmol) was added dropwise. After 15 minutes the flask was removed from the bath, the temperature was allowed to rise to 20° C. and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2-(4'-trifluoromethyl-phenoxy)-1-(2'-5'-tributylstannyl)thienyl)benzene having formula (c'):

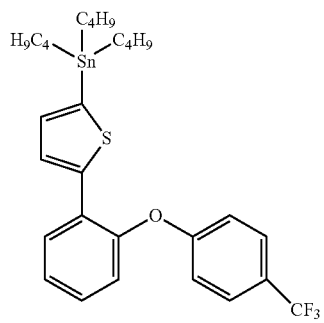

(c′)

was used as follows.

The residue comprising 2-(4′-trifluoromethylphenoxy)-1-[2′(5′-tributylstannyl)thienyl]-benzene having formula (c′) obtained as described above was dissolved in anhydrous toluene (Aldrich) (11 ml) in a 100 ml flask equipped with a magnetic stirrer, thermometer and cooling system, under an inert atmosphere, obtaining a solution to which was added 4,7-dibromo-5,6-diphenoxybenzothiadiazole having formula (a) obtained as described in Example 1 (0.207 g; 0.43 mmoles). After the air present had been removed through 3 vacuum/nitrogen cycles, tris(dibenzylideneacetone)dipalladium (Aldrich) (0.027 g; 0.03 mmol) and tris-o-tolylphosphine (Aldrich) (0.0125 g; 0.041 mmol) were added, obtaining a reaction mixture that was immersed in a bath preheated to 110° C. and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture, ratio 9/1 (v/v)]. The product obtained was recrystallized from a mixture of n-heptane (Aldrich)/dichloromethane (Aldrich) (ratio 9/1 (v/v)) obtaining 0.29 g of 2-(POP-4-CF3)-DTBOP having formula (7) (yield=70%).

Example 10 (Disclosure

Synthesis of 2-(POP-2-CF$_3$)-DTBOP Having Formula (8)

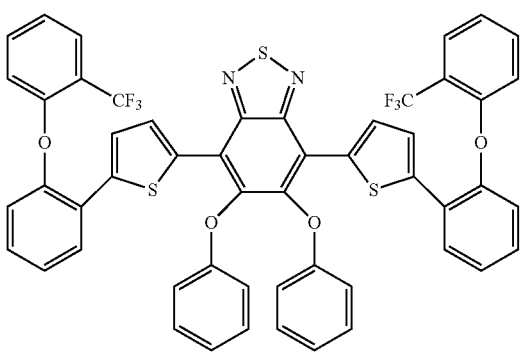

2-(POP-2-CF$_3$)-DTBOP (8)

(1) Synthesis of 2-(2′-trifluoromethylphenoxy)-1-bromobenzene Having Formula (d′

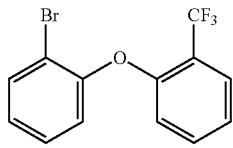

(d′)

The following were placed in a microwave vial: 2-bromophenol (Aldrich) (0.57 g; 0.38 ml; 3.3 mmol), 2-fluoro-1-trifluoromethylbenzene (Aldrich) (0.54 g; 0.42 ml; 3.3 mmol), potassium carbonate (Aldrich) (0.5 g; 3.6 mmol) and dimethylformamide (Aldrich) (5 ml). After the reaction mixture obtained had been shaken under a flow of argon the vial was closed with its special cap and placed in a 50 ml reactor: the reaction ramp was set from 25° C. to 190° C. over 4 minutes. The reaction mixture was kept in the reactor at 190° C. for 45 minutes, subsequently recovered, poured into distilled water (50 ml) and extracted with ethyl ether (Aldrich) (3×25 ml): the obtained organic phase was washed to neutral with distilled water (3×25 ml), and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)] to obtain 0.5 g of 2-(2′-trifluoromethylphenoxy)-1-bromobenzene having formula (d′) (yield=50%).

(2) Synthesis of 2-(2′-trifluoromethylphenoxy)-1-(2′-thienyl)benzene Having Formula (e′

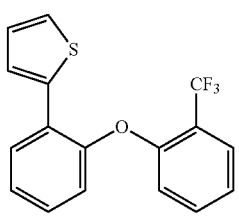

(e′)

2-Thienylboronic acid (Aldrich) (0.33 g; 2.6 mmol) and a 2 M aqueous solution of potassium carbonate (Aldrich) (1.18 g in 4.3 ml distilled water; 8.6 mmol) were added, under an inert atmosphere, to a 0.13 M solution of 2-(2′-trifluoromethylphenoxy)-1-bromobenzene having formula (d′) obtained as described above (0.67 g; 2.1 mmol) in anhydrous 1,4-dioxane (Aldrich) (16 ml) in a 100 ml flask equipped with a magnetic stirrer, thermometer and cooling system. After the air present had been removed through 3 vacuum/nitrogen cycles, tetrakis(triphenylphosphine)palladium (Aldrich) (0.05 g; 0.04 mmol) was added, obtaining a reaction mixture that was immersed in a bath preheated to 85'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by distillation at reduced pressure the residue obtained was added dropwise to 50 ml of methanol, obtaining a precipitate that was recovered by filtration and subsequently purified by elution on a silica gel chromatography column [eluent: n-heptane (Aldrich)] to obtain 0.35 g of 2-(2'-trifluoromethylphenoxy)-1-(2'-thienyl)benzene having formula (e') (yield=52%).

(3) Synthesis of 2-(POP-6-CF3)-DTBOP Having Formula (8)

n-Butyllithium (Aldrich) (1.6 M solution in hexane) (0.75 ml; 1.2 mmol) was added dropwise, under an inert atmosphere, to a 0.1 M solution of 2-(2'-trifluoromethylphenoxy)-1-(2'-thienyl)benzene having formula (e') obtained as described above (0.35 g; 1.1 mmol) in anhydrous tetrahydrofuran (Aldrich) (10 ml), at −78° C., in a 100 ml flask equipped with a magnetic stirrer and thermometer: the reaction mixture obtained was kept under stirring and the temperature was raised to −50° C. over 3 hours. After the flask had been placed in a bath containing acetone and dry ice at −78° C., tributylstannylchloride (Aldrich) (0.43 g; 0.4 ml; 1.3 mmol) was added dropwise. After 15 minutes the flask was removed from the bath, the temperature was allowed to rise to 20° C. and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2-(2'-trifluoromethyl-phenoxy)-1-[2'(5'-tributylstannyl)thienyl]benzene having formula (f'):

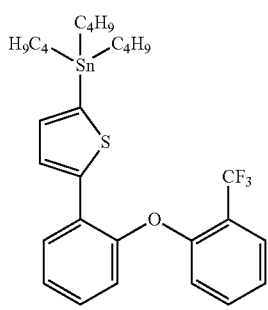

was used as follows.

In a 100 ml flask equipped with a magnetic stirrer, thermometer and cooling system, under an inert atmosphere, the residue comprising 2-(2'-trifluoromethylphenoxy)-1-[2'(5'-tributylstannyl)thienyl]benzene having formula (f') obtained as described above was dissolved in anhydrous toluene (Aldrich) (11 ml) to which 4,7-dibromo-5,6-diphenoxybenzothiadiazole having formula (a) obtained as described in Example 1 (0.207 g; 0.43 mmoles) was added. After the air present had been removed through 3 vacuum/nitrogen cycles, tris(dibenzylideneacetone)dipalladium (Aldrich) (0.010 g; 0.011 mmol) and tris-o-tolylphosphine (Aldrich) (0.0125 g; 0.041 mmol) were added, obtaining a reaction mixture that was immersed in a bath preheated to 110'C and kept, at said temperature, under stirring, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich) mixture ratio 9/1 (v/v)]. The product obtained was recrystallized from a n-heptane (Aldrich)/dichloromethane (Aldrich) mixture [ratio 9/1 (v/v)] obtaining 0.27 g of 2-(POP-6-CF3)-DTBOP having formula (8) (yield=66%).

Example 11 (Disclosure

Synthesis of 2,6-(POP-4-$C_8H_{17}$)-DTBOP Having Formula (9)

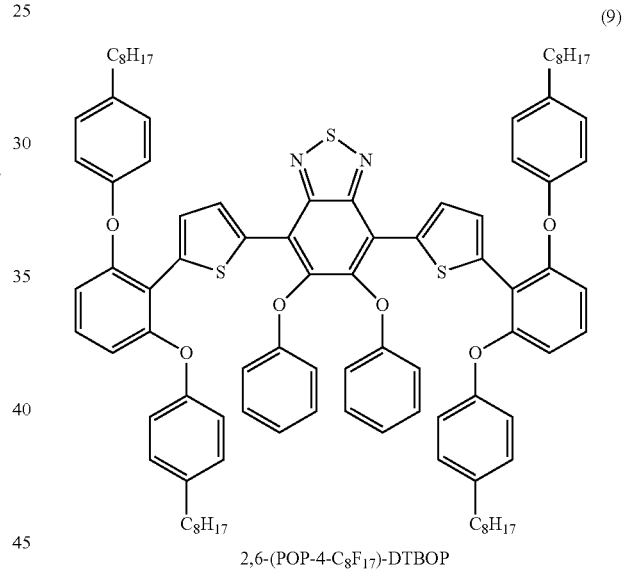

2,6-(POP-4-$C_8F_{17}$)-DTBOP

(1) Synthesis of 2,6-di-(4'-octylphenoxy)-1-bromobenzene Having Formula (g'

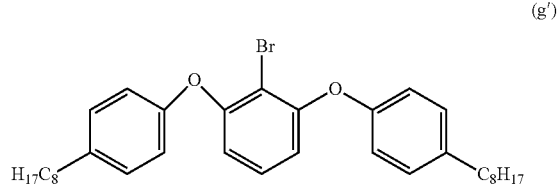

The following were placed in a microwave vial: 2,6-difluoro-1-bromobenzene (Aldrich) (0.5 g; 2.6 mmol), 4-octylphenol (1.2 g; 5.8 mmol), potassium carbonate (Aldrich) (1 g; 7.6 mmol) and N-methylpyrrolidone (Aldrich) (10 ml). After the reaction mixture obtained had been shaken under a flow of argon, the vial was closed with its special cap and placed in a 50 ml reactor: the reaction ramp was set from 25° C. to 220° C. over 4 minutes. The reaction mixture was kept in the reactor at 220'C for 2 hours, subsequently recovered, poured into distilled water (50 ml) and extracted with ethyl ether (Aldrich) (3×25 ml): the obtained organic phase was washed to neutral with distilled water (3×25 ml) and subsequently dehydrated on sodium sulfate (Aldrich). After the residual solvent had been removed by reduced pressure distillation the residue obtained was purified by elution on a silica gel chromatography column [eluent: n-heptane (Aldrich)] to obtain 0.57 g of 2,6-di-(4'-octylphenoxy)-1-bromobenzene having formula (g') (yield=38%).

(2) Synthesis of 2,6-(4'-octylphenoxy)-1-(2'-thienyl) benzene Having Formula (h'

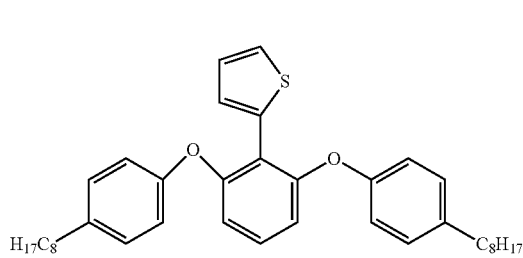

(h')

2-Tributylstannylthiophene (Aldrich) (0.45 g; 0.4 ml; 1.2 mmole) was added, under an inert atmosphere, to a 0.13 M solution of 2,6-di-(4'-octylphenoxy)-1-bromobenzene having formula (g') obtained as described above (0.57 g; 1 mmole) in anhydrous toluene (Aldrich) (10 ml) in a 100 ml flask equipped with a magnetic stirrer, thermometer and cooling system. After the air present had been removed through 3 vacuum/nitrogen cycles, tris(dibenzylideneacetone)dipalladium (Aldrich) (0.015 g; 0.016 mmol) and tris-o-tolylphosphine (Aldrich) (0.019 g; 0.06 mmol) were added, obtaining a reaction mixture that was immersed in a bath preheated to 85° C. and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by distillation at reduced pressure, the residue obtained was added dropwise to 200 ml of methanol, obtaining a precipitate that was recovered by filtration and subsequently purified by elution on a silica gel chromatography column [eluent: n-heptane (Aldrich)] to obtain 0.47 g of 2,6-(4'-octylphenoxy)-1-(2'-thienyl)benzene having formula (h') (yield=83%).

(3) Synthesis of 2,6-(POP-4-$C_8H_{17}$)-DTBOP Having Formula (9)

n-Butyllithium (Aldrich) (1.6 M solution in hexane) (1.4 ml; 2.2 mmol) was added dropwise, under an inert atmosphere, to a 0.1 M solution of 2,6-(4'-octylphenoxy)-1-(2'-thienyl)benzene having formula (h') obtained as described above (1.16 g; 2.04 mmol) in anhydrous tetrahydrofuran (Aldrich) (20.4 ml), at −78° C., in a 100 ml flask equipped with a magnetic stirrer and a thermometer: the reaction mixture obtained was kept under stirring and the temperature was raised to −50° C. over 3 hours. After the flask had been placed in a bath containing acetone and dry ice at −78° C., tributylstannylchloride (Aldrich) (0.8 g; 0.66 ml; 2.45 mmol) was added dropwise. After 15 minutes the flask was removed from the bath, the temperature was allowed to rise to 20'C and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2,6-(4'-octylphenoxy)-1-[2'(5'-tributylstannyl)thienyl]benzene having formula (i'):

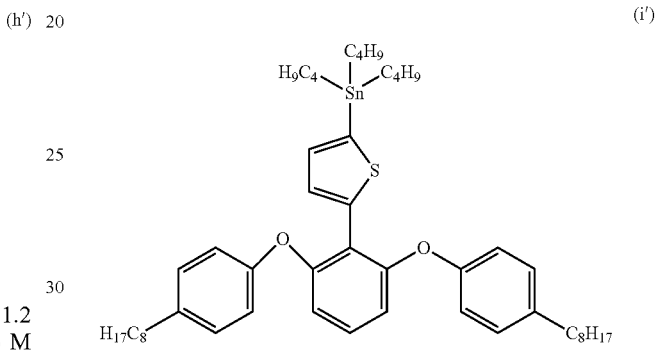

(i')

was used as follows.

In a 100 ml flask equipped with a magnetic stirrer, thermometer and cooling system, under an inert atmosphere, the residue comprising 2,6-(4'-octylphenoxy)-1-(2'(5'-tributylstannyl)thienyl)benzene having formula (i') obtained as described above was dissolved in anhydrous toluene (Aldrich) (10 ml) obtaining a solution to which was added 4,7-dibromo-5,6-diphenoxybenzothiadiazole having formula (a) obtained as described in Example 1 (0.207 g; 0.43 mmoles). After the air present had been removed through 3 vacuum/nitrogen cycles, tris(dibenzylideneacetone)dipalladium (Aldrich) (0.012 g; 0.013 mmol) and tris-o-tolylphosphine (Aldrich) (0.015 g; 0.05 mmol) were added, obtaining a reaction mixture that was immersed in a bath preheated to 110'C and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: n-heptane (Aldrich)/dichloromethane (Aldrich)/ethyl acetate (Aldrich) mixture 9/0.97/0.03 (v/v/v)]. The product obtained was recrystallized from a mixture of n-heptane (Aldrich)/dichloromethane (Aldrich) [ratio 9/1 (v/v)] to obtain 0.4 g of 2,6-(POP-4-$C_8H_{17}$)-DTBOP having formula (9) (yield=69%).

Example 12 (Disclosure

Synthesis of 2,6-(POP-4-C$_8$H$_{17}$)-(DTBOP-4-COOCH$_3$) Having Formula (10)

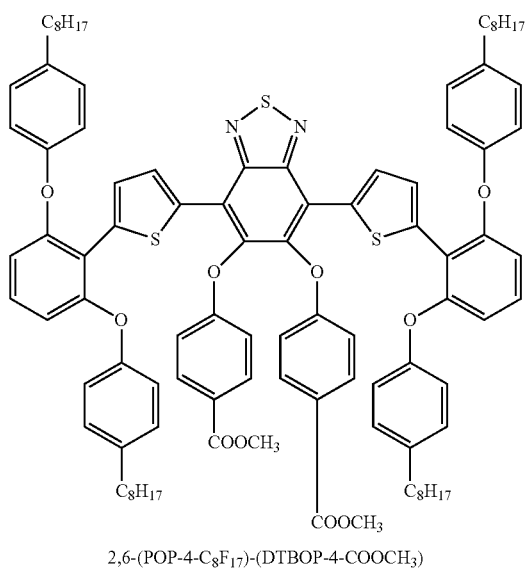

2,6-(POP-4-C$_8$F$_{17}$)-(DTBOP-4-COOCH$_3$)

n-Butyllithium (Aldrich) (1.6 M solution in hexane) (1.4 ml; 2.2 mmol) was added dropwise, under an inert atmosphere, to a 0.1 M solution of 2,6-(4'-octylphenoxy)-1-(2'-thienyl)benzene having formula (h') obtained as described above (1.16 g.; 2.04 mmol) in anhydrous tetrahydrofuran (Aldrich) (20.4 ml), at −78° C., in a 100 ml flask equipped with a magnetic stirrer and a thermometer: the reaction mixture obtained was kept under stirring and the temperature was raised to −50° C. over 3 hours. Subsequently the flask had been placed in a bath containing acetone and dry ice at −78° C., tributylstannylchloride (Aldrich) (0.8 g; 0.66 ml; 2.45 mmol) was added dropwise. After 15 minutes the flask was removed from the bath, the temperature was allowed to rise to 20° C. and the reaction mixture was kept, at said temperature, under stirring, for 12 hours. Subsequently, after a saturated solution of sodium bicarbonate had been added (Aldrich) (20 ml), the reaction mixture was extracted with ethyl ether (Aldrich) (3×25 ml): the obtained organic phase was washed with a saturated solution of sodium bicarbonate (Aldrich) (3×25 ml) and subsequently dehydrated on sodium sulfate (Aldrich). After the residual solvent had been removed by reduced pressure distillation the residue obtained comprising 2,6-(4'-octylphenoxy)-1-[2'-(5'-tributylstannyl)thienyl]benzene having formula (i'):

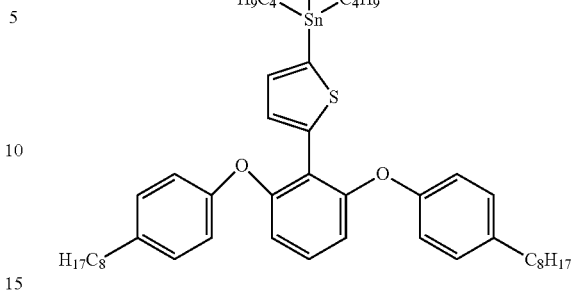

was used as follows.

In a 100 ml flask equipped with a magnetic stirrer, thermometer and cooling system, under an inert atmosphere, the residue comprising 2,6-(4'-octylphenoxy)-1-(2'(5'-tributylstannyl)thienyl)benzene having formula (i') obtained as described above was dissolved in anhydrous toluene (Aldrich) (10 ml) obtaining a solution to which was added 4,7-dibromo-5,6-di(4'-carbomethoxyphenoxy)benzothiadiazole having formula (d) obtained as described in Example 3 (0.237 g; 0.4 mmoles). After the air present had been removed through 3 vacuum/nitrogen cycles, tris(dibenzylideneacetone)dipalladium (Aldrich) (0.012 g; 0.013 mmol) and tris-o-tolylphosphine (Aldrich) (0.015 g; 0.05 mmol) were added, obtaining a reaction mixture that was immersed in a bath preheated to 110° C. and kept, under stirring, at said temperature, for 12 hours. The reaction mixture was subsequently poured into distilled water (50 ml) and extracted with dichloromethane (Aldrich) (3×25 ml): the obtained organic phase was washed to neutral with distilled water (3×25 ml) and subsequently dehydrated on sodium sulfate (Aldrich). After most of the residual solvent had been removed by reduced pressure distillation the residue obtained was added dropwise to 50 ml of methanol, obtaining a precipitate that was recovered by filtration and subsequently purified by elution on a silica gel chromatography column [eluent: mixture n-heptane (Aldrich)/dichloromethane (Aldrich)/ethyl acetate (Aldrich) 9/0.97/0.03 (v/v/v)]. The product obtained was recrystallized from a mixture of n-heptane (Aldrich)/dichloromethane (Aldrich) [ratio 9/1 (v/v)] to obtain 0.4 g of 2,6-(POP-4-C$_8$H$_{17}$)-(DTBOP-4-COOCH$_3$) having formula (10) (yield=64%).

Example 13 (Comparative 6 g of Altuglas VSUVT 100 (PMMA) polymethylmethacrylate and 49.5 mg of 4,7-di-(thien-2'-yl)-2,1,3-benzothiadiazole (DTB) were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25° C.), in a light current of air, for 24 hours. The result was a transparent sheet of yellow color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 4,7-di-(thien-2'-yl)-2,1,3-benzothiadiazole (DTB)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 5.69 mW (FIG. 1).

Figure 2:
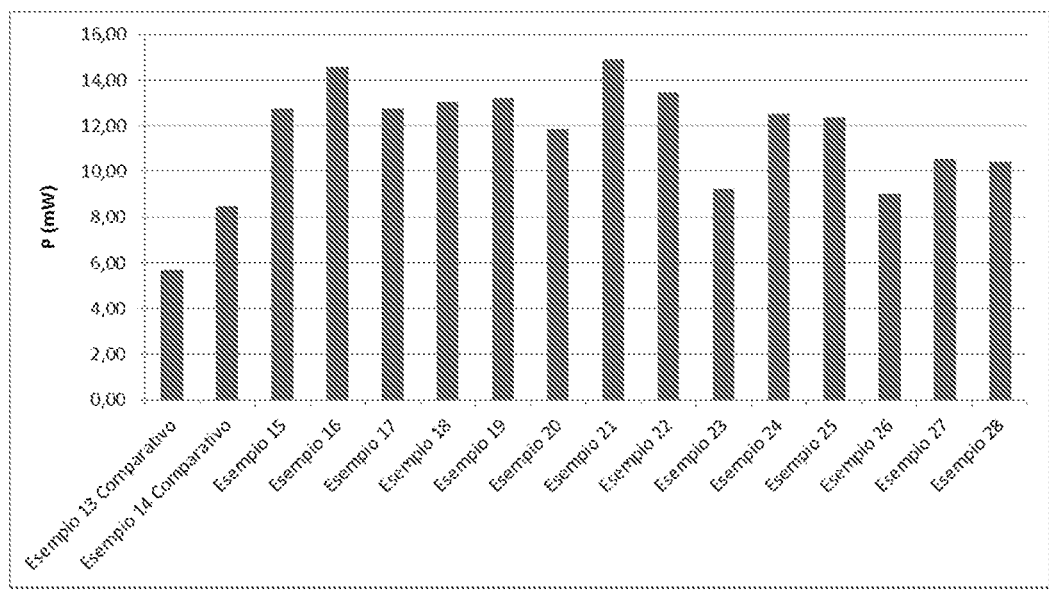
FIG. 2 shows a bar graph of power (P) generated by example and comparative example.

FIG. 2 shows the power (P) generated expressed in mW (shown as the ordinate) (the number of the example is shown as the abscissa).

Example 14 (Comparative 6 g of Altuglas VSUVT 100 (PMMA) polymethylmethacrylate and 87.1 mg of 5,6-diphenoxy-4,7-bis(2-thienyl)-2,1,3-benzothiadiazole having formula (Ia) (DTBOP) obtained as described in Example 1 of the international patent application WO 2016/046319 above were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25° C.) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 5,6-diphenoxy-4,7-bis(2-thienyl)-2,1,3-benzothiadiazole having formula (Ia)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 8.49 mW (FIG. 1).

FIG. 2 shows the power (P) generated expressed in mW (shown as the ordinate) (the number of the example is shown as the abscissa).

Example 15 (Disclosure 6 g of Altuglas VSUVT 100 (PMMA) polymethylmethacrylate and 85.2 mg of 2-POP-DTBOP having formula (1) obtained as described in Example 1 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2-POP-DTBOP having formula (1)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 12.76 mW (FIG. 1).

FIG. 2 shows the power (P) generated expressed in mW (shown as the ordinate) (the number of the example is shown as the abscissa).

Example 16 (Disclosure 6 g of Altuglas VSUVT 100 (PMMA) polymethylmethacrylate and 164.2 mg of 2-POP-DTBOP having formula (1) obtained as described in Example 1 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2-POP-DTBOP having formula (1)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 14.52 mW (FIG. 1).

FIG. 2 shows the power (P) generated expressed in mW (shown as the ordinate) (the number of the example is shown as the abscissa).

Example 17 (Disclosure 6 g of Altuglas VSUVT 100 (PMMA) polymethylmethacrylate and 165.2 mg of 2-POP-(DTBOP-4-COOCH$_3$) having formula (11) obtained as described in Example 3 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25° C.) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2-POP-(DTBOP-4-COOCH$_3$) having formula (11)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 12.74 mW (FIG. 1).

FIG. 2 shows the power (P) generated expressed in mW (shown as the ordinate) (the number of the example is shown as the abscissa).

Example 18 (Disclosure 6 g of Altuglas VSUVT 100 (PMMA) polymethylmethacrylate and 190.4 mg of 2,6-POP-DTBOP having formula (3) obtained as described in Example 4 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2,6-POP-DTBOP having formula (3)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 13.06 mW (FIG. 1).

FIG. 2 shows the power (P) generated expressed in mW (shown as the ordinate) (the number of the example is shown as the abscissa).

Example 19 (Disclosure 6 g of Altuglas VSUVT 100 (PMMA) polymethylmethacrylate and 180 mg of 2,4-POP-DTBOP having formula (4) obtained as described in Example 5 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2,4-POP-DTBOP having formula (4)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 13.23 mW (FIG. 1).

FIG. 2 shows the power (P) generated expressed in mW (shown as the ordinate) (the number of the example is shown as the abscissa).

Example 20 (Disclosure 6 g of Altuglas VSUVT 100 (PMMA) polymethylmethacrylate and 112 mg of 2,4,6-POP-DTBOP having formula (2) obtained as described in Example 6 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm$^2$ was subsequently applied to one of the edges of the polymer sheet.

The main face of the polymer plate [the one coated with the thin film containing the 2,4,6-POP-DTBOP having formula (2)] was subsequently illuminated with a light source with a power of 1 sol (1000 W/m$^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 11.88 mW (FIG. 1).

FIG. 2 shows the power (P) generated expressed in mW (shown as the ordinate) (the number of the example is shown as the abscissa).

Example 21 (Disclosure 6 g of Altuglas VSUVT 100 (PMMA) polymethylmethacrylate and 206 mg of 2,4,6-POP-DTBOP having formula (2) obtained as described in Example 6 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 $cm^2$ was subsequently applied to one of the edges of the polymer sheet.

The main face of the polymer plate [the one coated with the thin film containing the 2,4,6-POP-DTBOP having formula (2)] was subsequently illuminated with a light source with a power of 1 sol (1000 W/m2) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 14.9 mW (FIG. 1).

FIG. 2 shows the power (P) generated expressed in mW (shown as the ordinate) (the number of the example is shown as the abscissa).

Example 22 (Disclosure 6 g of Altuglas VSUVT 100 (PMMA) polymethylmethacrylate and 148.9 mg of 2-$CH_3$-4-POP-DTBOP having formula (5) obtained as described in Example 7 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 $cm^2$ was subsequently applied to one of the edges of the polymer sheet.

The main face of the polymer plate [the one coated with the thin film containing the 2-$CH_3$-4-POP-DTBOP having formula (5)] was subsequently illuminated with a light source with a power of 1 sol (1000 W/$m^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 13.48 mW (FIG. 1).

FIG. 2 shows the power (P) generated expressed in mW (shown as the ordinate) (the number of the example is shown as the abscissa).

Example 23 (Disclosure 6 g of Altuglas VSUVT 100 (PMMA) polymethylmethacrylate and 173.5 mg of 6-CF3-2-POP-DTBOP having formula (6) obtained as described in Example 8 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of yellow color provided by the film, the thickness of which was ranging from 100 μm to 50 μm.

An IXYS-KXOB22-12 photovoltaic cell with a surface area of 1.2 $cm^2$ was subsequently applied to one of the edges of the polymer sheet.

The main face of the polymer plate [the one coated with the thin film containing the 6-CF3-2-POP-DTBOP having formula (6)] was subsequently illuminated with a light source with a power of 1 sol (1000 W/$m^2$) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 9.22 mW (FIG. 1).

FIG. 2 shows the power (P) generated expressed in mW (shown as the ordinate) (the number of the example is shown as the abscissa).

Example 24 (Disclosure 6 g of Altuglas VSUVT 100 (PMMA) polymethylmethacrylate and 170.6 mg of 2-(POP-4-$CF_3$)-DTBOP having formula (7) obtained as described in Example 9 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm² was subsequently applied to one of the edges of the polymer sheet.

The main face of the polymer plate [the one coated with the thin film containing the 2-(POP-4-CF$_3$—)-DTBOP having formula (7)] was subsequently illuminated with a light source with a power of 1 sol (1000 W/m²) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 12.56 mW (FIG. 1).

FIG. 2 shows the power (P) generated expressed in mW (shown as the ordinate) (the number of the example is shown as the abscissa).

Example 25 (Disclosure 6 g of Altuglas VSUVT 100 (PMMA) polymethyl methacrylate and 170.6 mg of 2-(POP-2-CF$_3$)-DTBOP having formula (8) obtained as described in Example 10 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

A photovoltaic cell IXYS-KXOB22-12 with a surface area of 1.2 cm² was subsequently applied to one of the edges of the polymer sheet.

The main face of the polymer plate [the one coated with the thin film containing the 2-(POP-2-CF$_3$-)-DTBOP having formula (8)] was subsequently illuminated with a light source with a power of 1 sol (1000 W/m²) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 12.35 mW (FIG. 1).

FIG. 2 shows the power (P) generated expressed in mW (shown as the ordinate) (the number of the example is shown as the abscissa).

Example 26 (Disclosure 6 g of Altuglas VSUVT 100 (PMMA) polymethyl methacrylate and 292 mg of 2,6-(POP-4-C$_8$H$_{17}$)-DTBOP having formula (9) obtained as described in Example 11 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25° C.) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm² was subsequently applied to one of the edges of the polymer sheet.

The main face of the polymer plate [the one coated with the thin film containing the 2,6-(POP-4-C$_8$H$_{17}$)-DTBOP having formula (9)] was subsequently illuminated with a light source with a power of 1 sol (1000 W/m²) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 9.01 mW (FIG. 1).

FIG. 2 shows the power (P) generated expressed in mW (shown as the ordinate) (the number of the example is shown as the abscissa).

Example 27 (Disclosure 6 g of Altuglas VSUVT 100 (PMMA) polymethyl methacrylate and 260 mg of 2,6-(POP-4-C$_8$H$_{17}$)-(DTBOP-4-COOCH$_3$) having formula (10) obtained as described in Example 12 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25° C.) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm² was subsequently applied to one of the edges of the polymer sheet.

The main face of the polymer plate [the one coated with the thin film containing the 2,6-(POP-4-C$_8$H$_{17}$)-(DTBOP-4-COOCH$_3$) having formula (10)] was subsequently illuminated with a light source with a power of 1 sol (1000 W/m²) and the electrical power generated by the lighting effect was measured.

Power (P) was measured by illuminating a portion of the plate of dimensions 100 mm×90 mm at a distance (d) increasing from the edge to which the photovoltaic cell was fixed. These measurements at variable distance from the photovoltaic cell allow to quantify the contribution of waveguide, edge, diffusion and self-absorption effects.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 10.54 mW (FIG. 1).

FIG. 2 shows the power (P) generated expressed in mW (shown as the ordinate) (the number of the example is shown as the abscissa).

Example 28 (Disclosure 6 g of Altuglas VSUVT 100 (PMMA) polymethyl methacrylate and 151 mg of 2-POP-6-F-DTBOP having formula (12) obtained as described in Example 2 were dissolved in 30 ml of 1,2-dichlorobenzene (Aldrich). The obtained solution was subsequently uniformly deposited on a sheet of polymethylmethacrylate (dimensions 300 mm×90 mm×6 mm) using a film applicator of the "Doctor Blade" type and the solvent was allowed to evaporate at room temperature (25'C) in a light current of air for 24 hours. The result was a transparent sheet of orange color provided by the film, the thickness of which was ranging from 100 μm to 50 μm.

An IXYS-KXOB22-12 photovoltaic cell with a surface area of 1.2 cm² was subsequently applied to one of the edges of the polymer sheet.

The main face of the polymer plate [the one coated with the thin film containing the 2-POP-6-F-DTBOP having formula (12)] was subsequently illuminated with a light source with a power of 1 sol (1000 W/m²) and the electrical power generated by the lighting effect was measured.

Power (P) was measured by illuminating a portion of the plate of dimensions 100 mm×90 mm at a distance (d) increasing from the edge to which the photovoltaic cell was fixed. The contribution of waveguide, edge and self-absorption effects could be quantified through these measurements at a variable distance from the photovoltaic cell.

FIG. 1 shows the curve relating to the power (P) generated expressed in mW (shown as the ordinate) as a function of the distance (d) from the edge to which the photovoltaic cell was fixed, expressed in cm (shown as the abscissa).

It may be seen that, in the absence of edge effects, the average power generated was 10.46 mW (FIG. 1).

FIG. 2 shows the power (P) generated expressed in mW (shown as the ordinate) (the number of the example is shown as the abscissa).

The invention claimed is:

1. Disubstituted diaryloxybenzoheterodiazole compound having general formula (I):

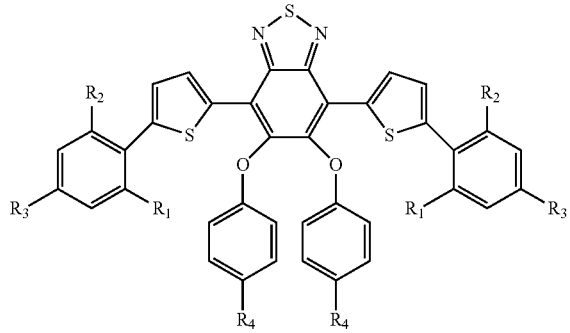

(I)

wherein:
 $R_1$, $R_2$ and $R_3$, which are the same as or different from each other, represent a hydrogen atom or represent a halogen atom or are selected from linear or branched $C_1$-$C_{12}$ alkyl groups optionally halogenated, phenoxy groups optionally substituted, provided that at least one of $R_1$, $R_2$ and $R_3$ is an optionally substituted phenoxy group, and, if $R_3$ is an phenoxy group optionally substituted, at least one of $R_1$ and $R_2$ is different from hydrogen;
 $R_4$, which are the same as or different from each other, represents a hydrogen atom or is selected from —COOR groups wherein R is selected from linear or branched $C_1$-$C_8$ alkyl groups.

2. Disubstituted diaryloxybenzoheterodiazole compound according to claim 1, wherein in said general formula (I):
 $R_1$, $R_2$ and $R_3$, which are the same as each other, are selected from phenoxy groups optionally substituted; and
 $R_4$, which are the same as each other, represents a hydrogen atom; or $R_1$ and $R_3$, which are the same as each other, represent a hydrogen atom and $R_2$ is selected from phenoxy groups optionally substitute; and
 $R_4$, which are the same as each other, represents a hydrogen atom; or
 $R_1$ and $R_2$, which are the same as each other, are selected from phenoxy groups optionally substituted, and $R_3$ represents a hydrogen atom; and
 $R_4$, which are the same as each other, represents a hydrogen atom; or
 $R_2$ and $R_3$, which are the same as each other, are selected from phenoxy groups optionally substituted and $R_1$ represents a hydrogen atom; and
 $R_4$, which are the same as each other, represents a hydrogen atom; or
 $R_1$ represents a hydrogen atom, $R_2$ is selected from $C_1$-$C_8$ linear or branched alkyl group optionally halogenated and $R_3$ is selected from phenoxy groups optionally substituted; and
 $R_4$, which are the same as each other, represents a hydrogen atom; or
 $R_1$ is selected from $C_1$-$C_8$, linear or branched alkyl groups optionally halogenated, $R_2$ is selected from phenoxy groups optionally substituted, and $R_3$ represents a hydrogen atom; and
 $R_4$, which are the same as each other, represents a hydrogen atom; or $R_1$ and $R_3$, which are the same as each other, represent a hydrogen atom and $R_2$ is selected from phenoxy groups optionally substituted; and $R_4$, which are the same as each other, represents a hydrogen atom; or $R_1$ and $R_3$, which are the same as each other, represent a hydrogen atom; $R_2$ is selected from phenoxy groups optionally substituted; and $R_4$, which are the same as each other, represents a hydrogen atom; or $R_1$ and $R_2$, which are the same as each other, are selected from phenoxy groups optionally substituted, and $R_3$ represents a hydrogen atom; and $R_4$, which are the same as each other, represents a hydrogen atom; or $R_1$ and $R_2$, which are the same as each other, are selected from phenoxy groups optionally substituted, and $R_3$ represents a hydrogen atom; and $R_4$, which are the same as each other, are selected from —COOR groups wherein R is selected from $C_1$-$C_8$ linear or branched alkyl groups; or $R_1$ and $R_3$, which are the same as each other, represent a hydrogen atom and $R_2$ is selected from phenoxy groups optionally substituted; and $R_4$, which are the same as each other, are selected from —COOR groups wherein R is selected from $C_1$-$C_8$ linear or branched alkyl groups; or $R_1$, which are the same as each other, represents a halogen atom, $R_2$ is selected from phenoxy groups optionally substituted, and $R_3$, which are the same as each other, represents a hydrogen atom; and $R_4$, which are the same as each other, represents a hydrogen atom.

3. Disubstituted diaryloxybenzoheterodiazole compound according to claim 2, wherein R is a $C_1$-$C_4$ linear or branched alkyl group optionally halogenated.

4. Disubstituted diaryloxybenzoheterodiazole compound according to claim 3, wherein R is a —COOCH$_3$ group.

5. Disubstituted diaryloxybenzoheterodiazole compound according to claim 1, wherein the halogen atom is selected from the group consisting of chlorine, bromine, fluorine, and iodine.

6. Disubstituted diaryloxybenzoheterodiazole compound according to claim 1, wherein the halogen atom is fluorine.

7. Disubstituted diaryloxybenzoheterodiazole compound according to claim 1, wherein the linear or branched $C_1$-$C_{12}$ alkyl groups optionally halogenated are linear or branched $C_1$-$C_8$ alkyl groups optionally halogenated.

8. Luminescent solar concentrator (LSC) including at least one disubstituted diaryloxybenzoheterodiazole compound having general formula (I) according to claim 1.

9. Photovoltaic device (or solar device) comprising at least one photovoltaic cell (or solar cell), and at least one luminescent solar concentrator (LSC) including at least one disubstituted diaryloxybenzoheterodiazole compound having general formula (I) according to claim 8.

* * * * *